United States Patent
Wiebe et al.

(10) Patent No.: US 11,147,275 B2
(45) Date of Patent: Oct. 19, 2021

(54) SUBSTITUTED TRIFLUOROMETHYLOXADIAZOLES FOR COMBATING PHYTOPATHOGENIC FUNGI

(71) Applicant: BASF SE, Ludwigshafen (DE)

(72) Inventors: Christine Wiebe, Ludwigshafen (DE); Wassilios Grammenos, Ludwigshafen (DE); Violeta Terteryan-Seiser, Ludwigshafen (DE); Maria Angelica Quintero-Palomar, Ludwigshafen (DE); Marcus Fehr, Limburgerhof (DE); Tobias Mentzel, Limburgerhof (DE); Ian Robert Craig, Ludwigshafen (DE); Georg Christoph Rudolf, Ludwigshafen (DE); Thomas Grote, Ludwigshafen (DE); Christian Winter, Ludwigshafen (DE); Ana Escribano Cuesta, Ludwigshafen (DE); Jan Klaas Lohmann, Ludwigshafen (DE); Michael Seet, Ludwigshafen (DE); Bernd Mueller, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/765,524

(22) PCT Filed: Nov. 7, 2018

(86) PCT No.: PCT/EP2018/080388
§ 371 (c)(1),
(2) Date: May 20, 2020

(87) PCT Pub. No.: WO2019/101511
PCT Pub. Date: May 31, 2019

(65) Prior Publication Data
US 2020/0315177 A1 Oct. 8, 2020

(30) Foreign Application Priority Data

Nov. 23, 2017 (EP) .................................... 17203288

(51) Int. Cl.
*A01N 43/82* (2006.01)
*C07D 413/10* (2006.01)
*C07D 413/12* (2006.01)
*A01N 43/80* (2006.01)

(52) U.S. Cl.
CPC ............. *A01N 43/82* (2013.01); *A01N 43/80* (2013.01); *C07D 413/10* (2013.01); *C07D 413/12* (2013.01)

(58) Field of Classification Search
CPC ...... A01N 43/80; A01N 43/82; C07D 413/10; C07D 413/12
See application file for complete search history.

(56) References Cited

U.S. PATENT DOCUMENTS 8,822,510 B2 * 9/2014 Das .................. C07D 271/06
514/364

FOREIGN PATENT DOCUMENTS

| WO | WO-2017/076935 A1 | 5/2017 | |
|----|----|----|----|
| WO | WO-2017/118689 A1 | 7/2017 | |
| WO | WO-2017/162868 A1 | 9/2017 | |
| WO | WO-2017162868 A1 * | 9/2017 | ............. A01N 25/28 |
| WO | WO-2017/211649 A1 | 12/2017 | |
| WO | WO-2017/211650 A1 | 12/2017 | |
| WO | WO-2017/211652 A1 | 12/2017 | |
| WO | WO-2018/114393 A1 | 6/2018 | |
| WO | WO-2018/153730 A1 | 8/2018 | |
| WO | WO-2018/184970 A1 | 10/2018 | |
| WO | WO-2018/188962 A1 | 10/2018 | |
| WO | WO-2018/202428 A1 | 11/2018 | |
| WO | WO-2018/202487 A1 | 11/2018 | |
| WO | WO-2018/202491 A1 | 11/2018 | |
| WO | WO-2018/219797 A1 | 12/2018 | |

(Continued)

OTHER PUBLICATIONS

European Search Report for EP Patent Application No. 17203288.0, dated Apr. 5, 2018, 3 pages.

(Continued)

*Primary Examiner* — Yong L Chu
(74) *Attorney, Agent, or Firm* — Marshall, Gerstein & Borun LLP

(57) ABSTRACT

The present invention relates to trifluoromethyloxadiazoles of the formula (I), or the N-oxides, or the agriculturally useful salts thereof; to a process for preparing compounds of the formula (I); to intermediates which are useful in the preparation of compounds of the formula (I); to the use of compounds of the formula (I) for controlling phytopathogenic fungi; to a method for combating phytopathogenic harmful fungi, which process comprises treating the fungi, the plants, the soil or seeds to be protected against fungal attack, with an effective amount of at least one compound of the formula (I), or an N-oxide, or an agriculturally acceptable salt thereof; and to agrochemical compositions comprising at least one compound of the formula (I), or an N-oxide, or an agriculturally acceptable salt thereof; and to agrochemical compositions further comprising seeds.

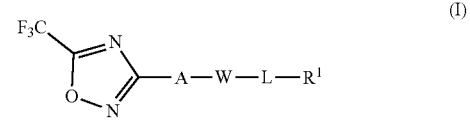

(I)

14 Claims, No Drawings

(56) References Cited

FOREIGN PATENT DOCUMENTS

| WO | WO-2018/234139 A1 | 12/2018 |
| WO | WO-2019/002158 A1 | 1/2019 |
| WO | WO-2019/020501 A1 | 1/2019 |
| WO | WO-2019/025250 A1 | 2/2019 |
| WO | WO-2019/038042 A1 | 2/2019 |
| WO | WO-2019/052932 A1 | 3/2019 |

OTHER PUBLICATIONS

International Application No. PCT/EP2018/080388, International Search Report and Written Opinion, dated Dec. 19, 2018.

* cited by examiner

SUBSTITUTED TRIFLUOROMETHYLOXADIAZOLES FOR COMBATING PHYTOPATHOGENIC FUNGI

The present invention relates to trifluoromethyloxadiazoles of the formula I, or the N-oxides, or the agriculturally useful salts thereof; to a process for preparing compounds of the formula I; to intermediates which are useful in the preparation of compounds of the formula I; to the use of compounds of the formula I for controlling phytopathogenic fungi; to a method for combating phytopathogenic harmful fungi, which process comprises treating the fungi, the plants, the soil or seeds to be protected against fungal attack, with an effective amount of at least one compound of the formula I, or an N-oxide, or an agriculturally acceptable salt thereof; and to agrochemical compositions comprising at least one compound of the formula I, or an N-oxide, or an agriculturally acceptable salt thereof; and to agrochemical compositions further comprising seeds.

Similar 5-trifluoromethyl-1,2,4-oxadiazoles are known as fungicides from WO 2017/162868 A1 and WO 2017/118689 A1.

In many cases, in particular at low application rates, the fungicidal activity of known fungicidal compounds is unsatisfactory. Based on this, it was an objective of the present invention to provide compounds having improved activity and/or a broader activity spectrum against phytopathogenic fungi. Another object of the present invention is to provide fungicides with improved toxicological properties. This objective is achieved by the oxadiazole compounds of the formula I, or the N-oxides, or their agriculturally useful salts for controlling phytopathogenic fungi.

The compounds according to the invention differ from those described in the closest prior art in the nature of group W.

Accordingly, the present invention relates to compounds of the formula I, or the N-oxides, or the agriculturally acceptable salts thereof,

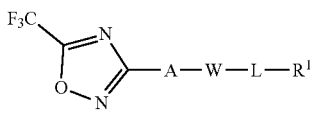

I wherein:
A is phenyl or a 5- or 6-membered aromatic heterocycle; wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein the phenyl ring or the aromatic heterocycle is unsubstituted or substituted with 1, 2, 3 or 4 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;
W is a 3- or 4-membered non-aromatic heterocycle containing as ring member atoms besides carbon atoms 1 nitrogen atom; wherein the heterocycle is bound to the group L through said nitrogen ring member atom; and wherein the heterocycle is bound to the group A through one of the carbon ring member atoms; and wherein the heterocycle is further unsubstituted or substituted with 1, 2, 3 or 4 identical or different radicals $R^W$; wherein
$R^W$ is halogen, cyano, $C_1$-$C_3$-alkyl, $C_1$-$C_3$-haloalkyl, $C_1$-$C_3$-alkoxy or $C_1$-$C_3$-haloalkoxy;
L is —C(=O)—, —C(=S)—, —S(=O)$_p$—, —C(=O)—O-#, —C(=O)NR$^2$-# or —C(=S)NR$^2$-#; wherein #denotes the position, which is bound to radical $R^1$; and wherein
p is 0, 1 or 2;
$R^2$ is hydrogen, formyl, $C_1$-$C_6$-alkyl, $C_2$-$C_6$-alkenyl, $C_2$-$C_6$-alkynyl, $C_3$-$C_5$-cycloalkyl, $C_1$-$C_6$-alkoxy or $C_1$-$C_6$-haloalkyl;
$R^1$ is hydrogen, $C_1$-$C_6$-alkyl, $C_2$-$C_6$-alkenyl, $C_3$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_3$-$C_{11}$-cycloalkyl, $C_3$-$C_{11}$-cycloalkenyl, $C_3$-$C_{11}$-cycloalkyl-$C_1$-$C_4$-alkyl, phenyl-$C_1$-$C_4$-alkyl, heterocyclyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein 1 or 2 carbon ring member atoms of the heterocycle may be replaced by 1 or 2 groups independently selected from C(=O) and C(=S); and wherein the heterocyclyl group in heterocyclyl-$C_1$-$C_4$-alkyl is a 3- to 10-membered saturated, partially unsaturated, mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein any of the aliphatic or cyclic groups $R^1$ are unsubstituted or substituted with 1, 2, 3 or up to the maximum possible number of identical or different groups $R^{1a}$; wherein $R^{1a}$ is halogen, cyano, $C_1$-$C_6$-alkyl, $C_1$-$C_6$-alkoxy or $C_1$-$C_6$-haloalkoxy.

Agriculturally acceptable salts of the compounds of the formula I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may be substituted with one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of acceptable acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydrobromic acid, sulfuric acid, phosphoric acid or nitric acid.

Compounds of the formula I can exist as one or more stereoisomers. The various stereoisomers include enantiomers, diastereomers, atropisomers arising from restricted rotation about a single bond of asymmetric groups and geometric isomers. They also form part of the subject matter of the present invention. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, e.g. a racemate, individual stereoisomers, or as an optically active form.

Compounds of the formula I can be present in different crystal modifications whose biological activity may differ. They also form part of the subject matter of the present invention.

In respect of the variables, the embodiments of the intermediates obtained during preparation of compounds I correspond to the embodiments of the compounds of formula I. The term "compounds I" refers to compounds of the formula I.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "oxo" refers to an oxygen atom =O, which is bound to a carbon atom or sulfur atom, thus forming, for example, a ketonyl —C(=O)— or sulfinyl —S(=O)— group.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2O_1$, $OCHCl_2$, $OOCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The terms "$C_3$-$C_{11}$-cycloalkyl-$C_1$-$C_4$-alkyl, heterocyclyl-$C_1$-$C_4$-alkyl, phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a cycloalkyl, heterocyclyl, phenyl or heteroaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above).

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_3$-$C_8$-cycloalkyl" refers to monocyclic saturated hydrocarbon radicals having 3 to 8 carbon ring members such as cyclopropyl ($C_3H_5$), cyclobutyl, cyclopentyl, cyclohexyl, cycloheptyl or cyclooctyl.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl). Further examples of bicyclic or tricyclic cycloalkyl radicals are found herein as embodiments $R^1.1$ to $R^1.26$.

The term "$C_1$-$C_6$-alkoxyimino-$C_1$-$C_4$-alkyl" refers to alkyl having 1 to 4 carbon atoms, wherein two hydrogen atoms of one carbon atom of the alkyl radical are replaced by a divalent $C_1$-$C_6$-alkoxyimino radical ($C_1$-$C_6$-alkyl-O—N=) as defined above.

The term "$C_2$-$C_6$-alkenyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkenyloxyimino radical ($C_2$-$C_6$-alkenyl-O—N=).

The term "$C_2$-$C_6$-alkynyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkynyloxyimino radical ($C_2$-$C_6$-alkynyl-O—N=).

The term "formyl" refers to a group —C(=O)H.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups $R^1$ are unsubstituted or substituted with . . . " refers to aliphatic groups, cyclic groups and groups, which contain an aliphatic and a cyclic moiety in one group, such as in, for example, $C_3$-$C_{11}$-cycloalkyl-$C_1$-$C_4$-alkyl or phenyl-$C_1$-$C_4$-alkyl; therefore, a group which contains an aliphatic and a cyclic moiety both of these moieties may be substituted or unsubstituted independently of each other.

The term "phenyl" refers to an aromatic ring systems including six carbon atoms (commonly referred to as benzene ring. In association with the group A the term "phenyl" is to be interpreted as a benzene ring or phenylene ring, which is attached to both, the oxadiazole moiety and the group L.

The term "heteroaryl", unless defined otherwise, refers to aromatic monocyclic or polycyclic ring systems including besides carbon atoms 1, 2, 3 or 4 heteroatoms independently selected from the group consisting of N, O and S as ring member atoms with the provision that the heterocycle cannot contain 2 contiguous atoms selected from O and S.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine;

and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-,-3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5- yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

In respect of the variables, the embodiments of the intermediates correspond to the embodiments of the compounds I. Preference is given to those compounds I and, where applicable, also to compounds of all subformulae provided herein, e. g. formulae I.1, I.2, I.A, I.B, I.C, I.D, I.E, I.F, I.G, I.H and I.J, wherein the variables A, $R^A$, W, $R^W$, L, p, $R^1$, $R^{1a}$, $R^2$, have independently of each other or more preferably in combination (any possible combination of 2 or more substituents as defined herein) the following meanings:

In one aspect of the invention group A is phenyl, which is unsubstituted or substituted with 1, 2, 3 or 4 identical or different groups $R^A$ as defined or preferably defined herein and wherein the group W is attached to the phenyl ring in para-position with regard to the oxadiazole group.

In one aspect of the invention A is phenyl, which is unsubstituted or substituted with 1, 2, 3 or 4 identical or different groups $R^A$ as defined or preferably defined herein and wherein the group W is attached to the phenyl ring in meta-position with regard to the oxadiazole group.

In a further aspect of the invention A is phenyl, which is substituted with 1 or 2 identical or different groups $R^A$ as defined or preferably defined herein and wherein the group W is attached to the phenyl ring in para-position with regard to the oxadiazole group.

In one embodiment A is a 6-membered aromatic heterocycle, wherein the ring member atoms of the aromatic heterocycle include besides carbon atoms 1 or 2 nitrogen atoms as ring member atoms; and wherein the aromatic heterocycle is unsubstituted or substituted with 1 or 2 identical or different groups $R^A$ as defined or preferably defined herein; particularly $R^A$ is chlorine, fluorine or methyl.

In a further embodiment A is a 6-membered aromatic heterocycle, wherein the ring member atoms of the aromatic heterocycle include besides carbon atoms 1 or 2 nitrogen atoms as ring member atoms; and wherein the aromatic heterocycle is unsubstituted or substituted with 1 or 2 identical or different groups $R^A$ as defined or preferably defined herein; particularly $R^A$ is chlorine, fluorine or methyl; and wherein the group W is attached to the 6-membered aromatic heterocycle in para-position with regard to the oxadiazole group.

In a further preferred embodiment A is a 5-membered aromatic heterocycle, in particular a thiophene ring, more particularly a 2,5-thiophenyl ring, wherein the ring member atoms of the heterocycle include besides carbon atoms 1, 2, 3 or 4 heteroatoms selected from N, O and S as ring member atoms with the provision that the heterocycle cannot contain 2 contiguous atoms selected from O and S; and wherein the cyclic groups A are unsubstituted or substituted with 1 or 2 identical or different groups $R^A$ as defined or preferably defined herein; particularly $R^A$ is chlorine, fluorine or methyl.

In one embodiment the invention relates to compounds of the formula I, wherein the moiety A is defined as in subformulae (A.1) to (A.30),

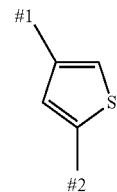

(A.1)

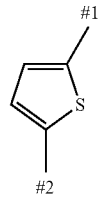

(A.2)

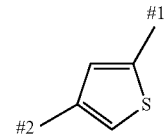

(A.3)

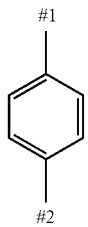

(A.4)

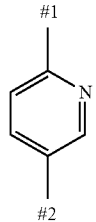

(A.5)

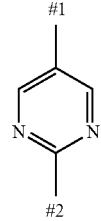

(A.6)

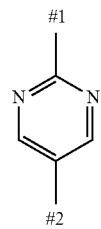

(A.7)

-continued
(A.8) 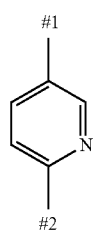
(A.9) 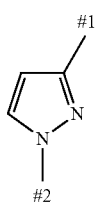
(A.10) 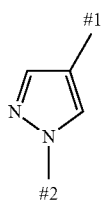
(A.11) 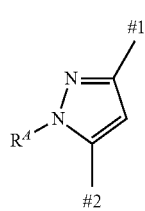
(A.12) 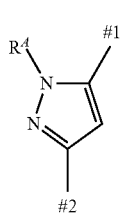
(A.13) 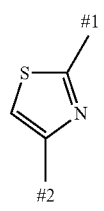
(A.14) 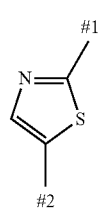
-continued
(A.15) 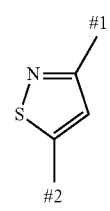
(A.16) 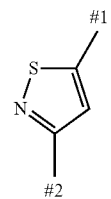
(A.17) 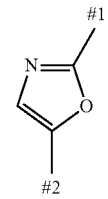
(A.18) 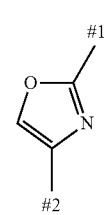
(A.19) 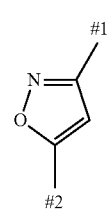
(A.20) 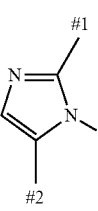
(A.21) 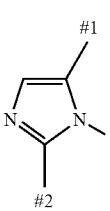

(A.22) 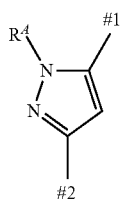

(A.23) 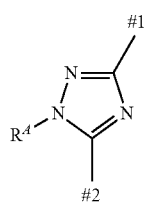

(A.24) 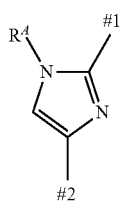

(A.25) 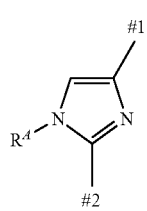

(A.26) 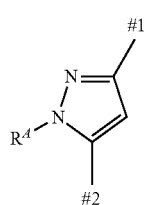

(A.27) 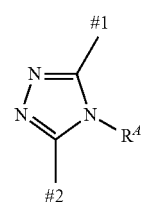

(A.28) 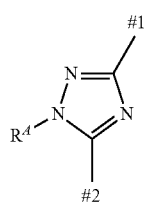

(A.29) 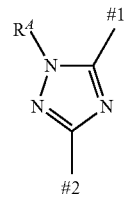

(A.30) 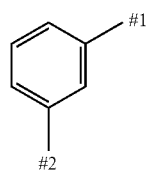

wherein #1 denotes the position, which is bound to the oxadiazole moiety and #2 denotes the position, which is connected to the W of compounds of the formula I; and wherein A is unsubstituted or substituted with 1 or 2 identical or different groups $R^A$ and wherein $R^A$ is as defined or preferably defined herein. In another embodiment A as defined in any one of subformulae (A.1) to (A.30) is unsubstituted or substituted with 1 or 2 identical or different groups $R^A$; and wherein $R^A$ is chlorine, fluorine or methyl. In a preferred embodiment A as defined in any one of subformulae (A.1) to (A.30) is unsubstituted.

In a preferred embodiment, $R^A$ is independently selected from the group consisting of halogen, $C_1$-$C_6$-alkyl or $C_3$-$C_8$-cycloalkyl. In another preferred embodiment, $R^A$ is independently selected from the group consisting of halogen, methyl or ethyl. More preferably $R^A$ is independently selected from the group consisting of halogen, in particular $R^A$ is fluorine.

Further embodiments with regard to the meaning of group W are as follows:

Embodiment W.1: W is selected from groups W.a, W.b and W.c,

W.a 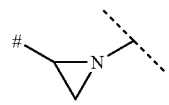

W.b 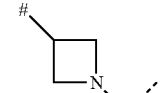

W.c 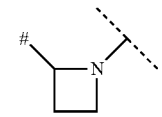

wherein # denotes the position, which is attached to the group A and the dashed line denotes the position, which is attached to $R^1$; and wherein W is further unsubstituted or substituted with 1, 2, 3 or 4 identical or different radicals $R^W$; wherein $R^W$ is halogen, cyano, $C_1$-$C_3$-alkyl, $C_1$-$C_3$-haloalkyl, $C_1$-$C_3$-alkoxy or $C_1$-$C_3$-haloalkoxy; preferably $R^W$ is halogen or $C_1$-$C_3$-alkyl.

Embodiment W.2: W is group W.b as defined in Embodiment W.1, wherein W is further unsubstituted or substituted with 1 or 2 identical or different radicals $R^W$; wherein $R^W$ is halogen, cyano, $C_1$-$C_3$-alkyl, $C_1$-$C_3$-haloalkyl, $C_1$-$C_3$-alkoxy or $C_1$-$C_3$-haloalkoxy; preferably $R^W$ is halogen or $C_1$-$C_3$-alkyl.

Embodiment W.3: W is group W.a as defined in Embodiment W.1, wherein W is further unsubstituted or substituted with 1 or 2 identical or different radicals $R^W$; wherein $R^W$ is halogen, cyano, $C_1$-$C_3$-alkyl, $C_1$-$C_3$-haloalkyl, $C_1$-$C_3$-alkoxy or $C_1$-$C_3$-haloalkoxy; preferably $R^W$ is halogen or $C_1$-$C_3$-alkyl.

Further embodiments with regard to the meaning of group L are as follows:

Embodiment L.1: L is —C(=O)—, —C(=S)— or —S(=O)$_p$—; and wherein p is 0, 1 or 2.

Embodiment L.2: L is —S(=O)$_2$—.

Embodiment L.3: L is —C(=O)— or —C(=S)—.

Embodiment L.4: L is —C(=O)—O-#, —C(=O)NR$^2$-# or —C(=S)NR$^2$-#; wherein #denotes the position, which is bound to radical $R^1$; and wherein $R^2$ is hydrogen, formyl, $C_1$-$C_6$-alkyl, $C_2$-$C_6$-alkenyl, $C_2$-$C_6$-alkynyl, $C_3$-$C_5$-cycloalkyl, $C_1$-$C_6$-alkoxy or $C_1$-$C_6$-haloalkyl.

Embodiment L.5: L is —C(=O)NR$^2$-#; wherein #denotes the position, which is bound to radical $R^1$; and wherein $R^2$ is hydrogen, formyl, methyl, ethyl, n-propyl, iso-propyl, n-butyl, sec-butyl, iso-butyl, tert-butyl, methoxy, ethyoxy, n-propyloxy, iso-propyloxy, cyclopropyl, cyclopropyl-CH$_2$—, allyl or propargyl.

Further embodiments with regard to the meaning of radical $R^1$ are as follows:

Embodiment 1.1: $R^1$ is hydrogen, $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_3$-$C_8$-cycloalkyl, $C_3$-$C_8$-cycloalkenyl, $C_3$-$C_8$-cycloalkyl-$C_1$-$C_4$-alkyl, phenyl-$C_1$-$C_4$-alkyl, heteroaryl-$C_1$-$C_4$-alkyl-, phenyl, or a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein the heteroaryl group in heteroaryl-$C_1$-$C_4$-alkyl is a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein any of the aliphatic or cyclic groups $R^1$ are unsubstituted or substituted with 1, 2, 3 or up to the maximum possible number of identical or different radicals selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

Embodiment 1.2: $R^1$ is hydrogen, $C_1$-$C_6$-alkyl, $C_2$-$C_6$-alkenyl, $C_3$-$C_6$-alkynyl $C_3$-$C_{11}$-cycloalkyl.

Embodiment 1.3: $R^1$ is hydrogen, methyl, ethyl, n-propyl, iso-propyl, n-butyl, iso-butyl, sec-butyl, tert-butyl or cyclopropyl.

Embodiment 1.4: $R^1$ is phenyl or heteroaryl; and wherein the heteroaryl group is a 5- or 6-membered aromatic heterocycle, wherein the ring includes besides carbon atoms 1, 2, 3 or 4 heteroatoms selected from N, O and S as ring member atoms with the provision that the heterocycle cannot contain 2 contiguous atoms selected from O and S; and wherein any of the cyclic groups are unsubstituted or substituted with 1, 2, 3 or up to the maximum possible number of identical or different radicals selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

Embodiment 1.5: $R^1$ is $C_3$-$C_{11}$-cycloalkyl or $C_3$-$C_{11}$-cycloalkenyl; and wherein the cyclic group is unsubstituted or substituted with 1, 2, 3 or up to the maximum possible number of identical or different radicals selected from the group consisting of halogen, oxo, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

Embodiment 1.6: $R^1$ is $C_1$-$C_6$-alkyl; and wherein the alkyl group is unsubstituted or substituted with 1, 2, 3 or up to the maximum possible number of identical or different radicals selected from the group consisting of halogen, oxo, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

Embodiment 1.7: $R^1$ is difluoromethyl, trifluoromethyl, 2,2-difluoroethyl, 2,2,2-trifluoroethyl, 2-chloro-2-fluoroethyl, 2-chloro-2,2-difluoroethyl, 2,2,2-trichloroethyl and pentafluoroethyl, 3,3,3-trifluoropropyl, $CH_2CF_2CF_3$ or $CF_2CF_2CF_5$, $CH(CH_3)CF_3$, $CH_2CF_2CH_3$, $CH_2C(CH_3)_2F$, $CH_2CH(CH_3)CF_3$ or $CH_2C(CH_3)_2CF_3$.

Embodiment 1.8: $R^1$ is $C_1$-$C_6$-alkoxyimino-$C_1$-$C_4$-alkyl, $C_2$-$C_6$-alkenyloxyimino-$C_1$-$C_4$-alkyl or $C_2$-$C_6$-alkynyloxyimino-$C_1$-$C_4$-alkyl.

Embodiment 1.9: $R^1$ is selected from the group consisting of radicals $R^{1.1}$ to $R^{1.26}$ below, particularly from $R^{1.1}$ to $R^{1.18}$, which are further unsubstituted or substituted with 1 or 2 radicals selected from the group consisting of methyl, ethyl, oxo, hydroxyl and halogen; and wherein "#C" indicates the carbon atom, which is attached to the remainder of the compounds of formula I.

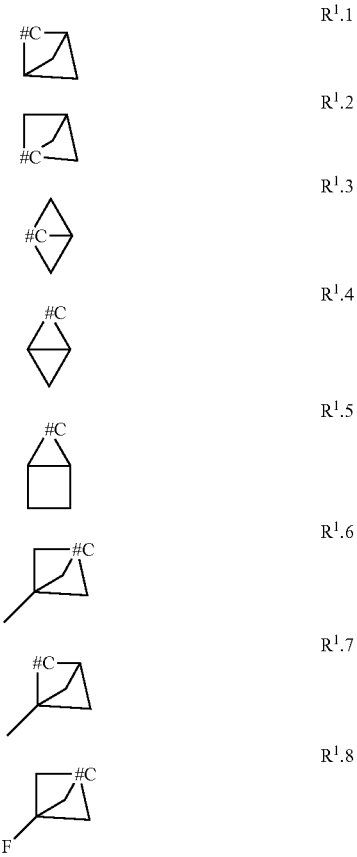

R¹.9 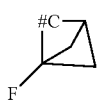

R¹.10 

R¹.11 

R¹.12 

R¹.13 

R¹.14 

R¹.15 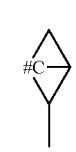

R¹.16 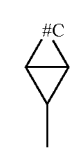

R¹.17 

R¹.18 

R¹.19 

R¹.20 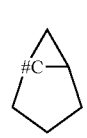

R¹.21 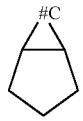

R¹.22 

R¹.23 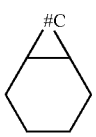

R¹.24 

R¹.25 

R¹.26 

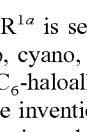

In one embodiment $R^{1a}$ is selected from the group consisting of halogen, oxo, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl. In another aspect of the invention Ria is selected from the group consisting of fluorine, chlorine, oxo, cyano, methyl, ethyl, methoxy, trifluoromethyl, trifluoromethoxy, difluoromethyl, difluoromethoxy and cyclopropyl.

In a preferred aspect of the invention $R^{1a}$ is selected from the group consisting of halogen, oxo, $C_1$-$C_6$-alkyl and $C_3$-$C_8$-cycloalkyl; particularly from oxo, methyl, ethyl, fluorine and chlorine; more particularly from fluorine and chlorine.

In further aspects of the present invention, the embodiments E.1 to E.84 listed in Table E represent preferred combinations of the embodiments, which are defined herein above for each of the variables W, L, and $R^1$.

TABLE E

| Embodiment | W | L | R¹ |
|---|---|---|---|
| E.1 | W.1 | L.1 | 1.1 |
| E.2 | W.1 | L.1 | 1.2 |
| E.3 | W.1 | L.1 | 1.4 |
| E.4 | W.1 | L.1 | 1.5 |
| E.5 | W.1 | L.1 | 1.6 |
| E.6 | W.1 | L.1 | 1.8 |
| E.7 | W.1 | L.1 | 1.9 |
| E.8 | W.1 | L.2 | 1.1 |
| E.9 | W.1 | L.2 | 1.2 |
| E.10 | W.1 | L.2 | 1.4 |
| E.11 | W.1 | L.2 | 1.5 |
| E.12 | W.1 | L.2 | 1.6 |

TABLE E-continued

| Embodiment | W | L | R$^1$ |
|---|---|---|---|
| E.13 | W.1 | L.2 | 1.8 |
| E.14 | W.1 | L.2 | 1.9 |
| E.15 | W.1 | L.3 | 1.1 |
| E.16 | W.1 | L.3 | 1.2 |
| E.17 | W.1 | L.3 | 1.4 |
| E.18 | W.1 | L.3 | 1.5 |
| E.19 | W.1 | L.3 | 1.6 |
| E.20 | W.1 | L.3 | 1.8 |
| E.21 | W.1 | L.3 | 1.9 |
| E.22 | W.1 | L.4 | 1.1 |
| E.23 | W.1 | L.4 | 1.2 |
| E.24 | W.1 | L.4 | 1.4 |
| E.25 | W.1 | L.4 | 1.5 |
| E.26 | W.1 | L.4 | 1.6 |
| E.27 | W.1 | L.4 | 1.8 |
| E.28 | W.1 | L.4 | 1.9 |
| E.29 | W.2 | L.1 | 1.1 |
| E.30 | W.2 | L.1 | 1.2 |
| E.31 | W.2 | L.1 | 1.4 |
| E.32 | W.2 | L.1 | 1.5 |
| E.33 | W.2 | L.1 | 1.6 |
| E.34 | W.2 | L.1 | 1.8 |
| E.35 | W.2 | L.1 | 1.9 |
| E.36 | W.2 | L.2 | 1.1 |
| E.37 | W.2 | L.2 | 1.2 |
| E.38 | W.2 | L.2 | 1.4 |
| E.39 | W.2 | L.2 | 1.5 |
| E.40 | W.2 | L.2 | 1.6 |
| E.41 | W.2 | L.2 | 1.8 |
| E.42 | W.2 | L.2 | 1.9 |
| E.43 | W.2 | L.3 | 1.1 |
| E.44 | W.2 | L.3 | 1.2 |
| E.45 | W.2 | L.3 | 1.4 |
| E.46 | W.2 | L.3 | 1.5 |
| E.47 | W.2 | L.3 | 1.6 |
| E.48 | W.2 | L.3 | 1.8 |
| E.49 | W.2 | L.3 | 1.9 |
| E.50 | W.2 | L.4 | 1.1 |
| E.51 | W.2 | L.4 | 1.2 |
| E.52 | W.2 | L.4 | 1.4 |
| E.53 | W.2 | L.4 | 1.5 |
| E.54 | W.2 | L.4 | 1.6 |
| E.55 | W.2 | L.4 | 1.8 |
| E.56 | W.2 | L.4 | 1.9 |
| E.57 | W.3 | L.1 | 1.1 |
| E.58 | W.3 | L.1 | 1.2 |
| E.59 | W.3 | L.1 | 1.4 |
| E.60 | W.3 | L.1 | 1.5 |
| E.61 | W.3 | L.1 | 1.6 |
| E.62 | W.3 | L.1 | 1.8 |
| E.63 | W.3 | L.1 | 1.9 |
| E.64 | W.3 | L.2 | 1.1 |
| E.65 | W.3 | L.2 | 1.2 |
| E.66 | W.3 | L.2 | 1.4 |
| E.67 | W.3 | L.2 | 1.5 |
| E.68 | W.3 | L.2 | 1.6 |
| E.69 | W.3 | L.2 | 1.8 |
| E.70 | W.3 | L.2 | 1.9 |
| E.71 | W.3 | L.3 | 1.1 |
| E.72 | W.3 | L.3 | 1.2 |
| E.73 | W.3 | L.3 | 1.4 |
| E.74 | W.3 | L.3 | 1.5 |
| E.75 | W.3 | L.3 | 1.6 |
| E.76 | W.3 | L.3 | 1.8 |
| E.77 | W.3 | L.3 | 1.9 |
| E.78 | W.3 | L.4 | 1.1 |
| E.79 | W.3 | L.4 | 1.2 |
| E.80 | W.3 | L.4 | 1.4 |
| E.81 | W.3 | L.4 | 1.5 |
| E.82 | W.3 | L.4 | 1.6 |
| E.83 | W.3 | L.4 | 1.8 |
| E.84 | W.3 | L.4 | 1.9 |

In one embodiment, the invention relates to compounds of the formula I, or the N-oxides, or the agriculturally acceptable salts thereof, wherein A is a group selected from subformulae (A.1) to (A.30); and wherein the phenyl ring or the aromatic heterocycle is unsubstituted or substituted with 1 or 2 identical or different groups R$^A$; wherein
  R$^A$ is halogen, cyano, C$_1$-C$_6$-alkyl, C$_1$-C$_6$-haloalkyl, C$_1$-C$_6$-alkoxy or C$_1$-C$_6$-haloalkoxy;
W is selected from groups W.a, W.b and W.c as defined herein; and wherein W is further unsubstituted or substituted with 1, 2, 3 or 4 identical or different radicals R$^W$; wherein R$^W$ is halogen, cyano, C$_1$-C$_3$-alkyl, C$_1$-C$_3$-haloalkyl, C$_1$-C$_3$-alkoxy or C$_1$-C$_3$-haloalkoxy;
L is —C(═O)—, —C(═S)—, —S(═O)$_p$—, —C(═O)—O-#, —C(═O)NR$^2$-# or —C(═S)NR$^2$-#; wherein #denotes the position, which is bound to radical R$^1$; and wherein
  p is 0, 1 or 2;
  R$^2$ is hydrogen, formyl, C$_1$-C$_6$-alkyl, C$_2$-C$_6$-alkenyl, C$_2$-C$_6$-alkynyl, C$_3$-C$_5$-cycloalkyl, C$_1$-C$_6$-alkoxy or C$_1$-C$_6$-haloalkyl;
R$^1$ is hydrogen, C$_1$-C$_6$-alkyl, C$_2$-C$_6$-alkenyl, C$_2$-C$_6$-alkynyl, C$_1$-C$_6$-alkoxyimino-C$_1$-C$_4$-alkyl, C$_2$-C$_6$-alkenyloxyimino-C$_1$-C$_4$-alkyl, C$_2$-C$_6$-alkynyloxyimino-C$_1$-C$_4$-alkyl, C$_3$-C$_8$-cycloalkyl, C$_3$-C$_8$-cycloalkenyl, C$_3$-C$_8$-cycloalkyl-C$_1$-C$_4$-alkyl, phenyl-C$_1$-C$_4$-alkyl, heteroaryl-C$_1$-C$_4$-alkyl-, phenyl, or a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein the heteroaryl group in heteroaryl-C$_1$-C$_4$-alkyl is a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein any of the aliphatic or cyclic groups R$^1$ are unsubstituted or substituted with 1, 2, 3 or up to the maximum possible number of identical or different radicals selected from the group consisting of halogen, cyano, C$_1$-C$_6$-alkyl, C$_1$-C$_6$-haloalkyl, C$_1$-C$_6$-alkoxy, C$_1$-C$_6$-haloalkoxy and C$_3$-C$_8$-cycloalkyl.

In another embodiment, the invention relates to compounds of the formula I, or the N-oxides, or the agriculturally acceptable salts thereof, wherein A is a phenyl ring; and wherein the phenyl ring is unsubstituted or substituted with 1 or 2 identical or different groups R$^A$; wherein
  R$^A$ is halogen, cyano, C$_1$-C$_6$-alkyl, C$_1$-C$_6$-haloalkyl, C$_1$-C$_6$-alkoxy or C$_1$-C$_6$-haloalkoxy;
W is selected from groups W.a, W.b and W.c as defined herein; and wherein W is further unsubstituted or substituted with 1, 2, 3 or 4 identical or different radicals R$^W$; wherein R$^W$ is halogen, cyano, C$_1$-C$_3$-alkyl, C$_1$-C$_3$-haloalkyl, C$_1$-C$_3$-alkoxy or C$_1$-C$_3$-haloalkoxy;
L is —C(═O)—, —C(═S)—, —S(═O)$_p$—, —O(═O)—O-#, —C(═O)NR$^2$-# or —C(═S)NR$^2$-#; wherein #denotes the position, which is bound to radical R$^1$; and wherein
  p is 1 or 2;
  R$^2$ is hydrogen, formyl, C$_1$-C$_6$-alkyl, C$_2$-C$_6$-alkenyl, C$_2$-C$_6$-alkynyl, C$_3$-C$_5$-cycloalkyl, C$_1$-C$_6$-alkoxy or C$_1$-C$_6$-haloalkyl;

R$^1$ is hydrogen, C$_1$-C$_6$-alkyl, C$_2$-C$_6$-alkenyl, C$_3$-C$_6$-alkynyl or C$_3$-C$_8$-cycloalkyl; preferably hydrogen, methyl, ethyl, n-propyl, iso-propyl, n-butyl, iso-butyl, sec-butyl, tert-butyl or cyclopropyl.

In one embodiment, the invention relates to compounds of the formula I.1 or to compounds of the formula I.2, or the N-oxides, or the agriculturally acceptable salts thereof,

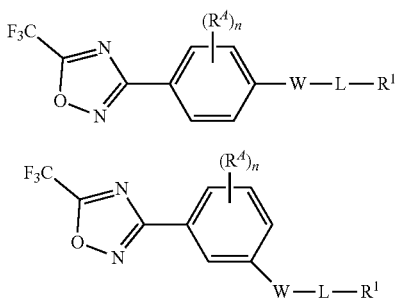

wherein n is 0, 1 or 2; and wherein the meaning of the variables W, R$^W$, L, R$^1$ and R$^2$ are as defined herein for compounds of the formula I or as defined in embodiments E.1 to E.84 in Table E; and wherein R$^A$ is as defined or preferably defined herein for compounds of the formula I.

A preferred embodiment relates to compounds of the formula I.1 or to compounds of the formula I.2 as defined above, wherein the meaning of the variables W, R$^W$, L, R$^1$ and R$^2$ are as defined herein for compounds of the formula I or as defined in embodiments E.1 to E.84 in Table E; and wherein n is 0 or 1 and R$^A$ is fluorine.

In a further embodiment the invention relates to compounds of formula I.1, or the N-oxides, or the agriculturally acceptable salts thereof, wherein:
R$^A$ is fluorine;
n is 0 or 1;
W is selected from groups W.a, W.b and W.c as defined herein; wherein W is further unsubstituted or substituted with 1 or 2 identical or different radicals R$^W$; wherein
  R$^W$ is halogen, cyano, C$_1$-C$_3$-alkyl, C$_1$-C$_3$-haloalkyl, C$_1$-C$_3$-alkoxy or C$_1$-C$_3$-haloalkoxy;
L is —C(=O)—, —C(=S)—, —S(=O)—, —S(=O)$_2$—, —C(=O)—O-#, —C(=O)NR$^2$-# or —C(=S)NR$^2$-#; wherein #denotes the position, which is bound to radical R$^1$; and wherein
  R$^2$ is hydrogen, formyl, C$_1$-C$_6$-alkyl, C$_2$-C$_6$-alkenyl, C$_2$-C$_6$-alkynyl, C$_3$-C$_5$-cycloalkyl, C$_1$-C$_6$-alkoxy or C$_2$-C$_6$-haloalkyl;
R$^1$ is as defined herein for compounds of the formula I, or as preferably defined in any one of Embodiments 1.1 to 1.14.

In a further embodiment the invention relates to compounds of formula I.1, or the N-oxides, or the agriculturally acceptable salts thereof, wherein:
n is 0;
W is selected from groups W.a, W.b and W.c as defined herein; wherein W is further unsubstituted or substituted with 1 or 2 identical or different radicals R$^W$; wherein
  R$^W$ is halogen or C$_1$-C$_3$-alkyl;
L is —C(=O)— or —S(=O)$_2$—;
R$^1$ is hydrogen, C$_1$-C$_6$-alkyl, C$_2$-C$_6$-alkenyl, C$_3$-C$_6$-alkynyl or C$_3$-C$_{11}$-cycloalkyl.

In a further embodiment the invention relates to compounds of formula I.1, or the N-oxides, or the agriculturally acceptable salts thereof, wherein:
n is 0;
W is a group W.b as defined herein; wherein W is further unsubstituted or substituted with 1 or 2 identical or different radicals R$^W$; wherein
  R$^W$ is halogen or C$_1$-C$_3$-alkyl;
L is —C(=O)— or —S(=O)$_2$—;
R$^1$ is as defined herein for compounds of the formula I, or as preferably defined in any one of Embodiments 1.1 to 1.14.

In a further embodiment the invention relates to compounds of formula I.1, or the N-oxides, or the agriculturally acceptable salts thereof, wherein:
n is 0;
W is a group W.b as defined herein; wherein W is further unsubstituted or substituted with 1 or 2 identical or different radicals R$^W$; wherein
  R$^W$ is halogen or C$_1$-C$_3$-alkyl;
L is —C(=O)—, —C(=S)—, —S(=O)—, —S(=O)$_2$—, —C(=O)—O-#, —C(=O)NR$^2$-# or —C(=S)NR$^2$-#; wherein #denotes the position, which is bound to radical R$^1$; and wherein
  R$^2$ is hydrogen, formyl, C$_1$-C$_6$-alkyl, C$_2$-C$_6$-alkenyl, C$_2$-C$_6$-alkynyl, C$_3$-C$_5$-cycloalkyl, C$_1$-C$_6$-alkoxy or C$_2$-C$_6$-haloalkyl;
R$^1$ is hydrogen, C$_1$-C$_6$-alkyl, C$_2$-C$_6$-alkenyl, C$_3$-C$_6$-alkynyl or C$_3$-C$_{11}$-cycloalkyl; preferably hydrogen, methyl, ethyl, n-propyl, iso-propyl, n-butyl, iso-butyl, sec-butyl, tert-butyl or cyclopropyl.

In a further embodiment the invention relates to compounds of formula I.1, or the N-oxides, or the agriculturally acceptable salts thereof, wherein:
n is 0;
W is a group W.b as defined herein; wherein W is further unsubstituted;
L is —C(=O)— or —S(=O)$_2$—;
R$^1$ is hydrogen, methyl, ethyl, n-propyl, iso-propyl, n-butyl, iso-butyl, sec-butyl, tert-butyl or cyclopropyl.

In one embodiment the present invention relates to compounds of the formulae I.A, I.B and I.C, wherein the radicals L and R$^1$ are as defined or preferably defined herein:

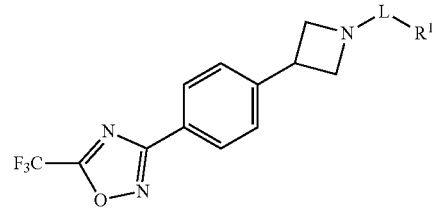

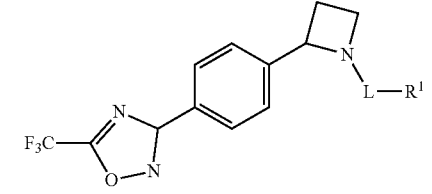

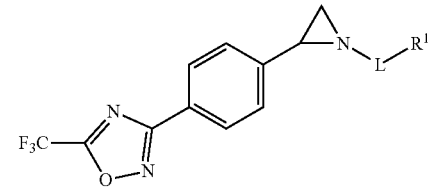

Preference is given to compounds of the formula I, which are compiled in Tables 1 to 3 below, and which may be used according to the invention.

Table 1: Compounds of the formula I.A, in which L and $R^1$ for each individual compound corresponds in each case to one line A-1 to A-72 of Table A (compounds I.A.A-1 to I.A.A-72). This means, for example, that a compound of formula I.A, wherein L is —C(=O)— and $R^1$ is methyl (corresponding to the definition A-49 in Table A) is named I.A.A-49.

Table 2: Compounds of the formula I.B, in which L and $R^1$ for each individual compound corresponds in each case to one line A-1 to A-72 of Table A (compounds I.B.A-1 to I.B.A-72).

Table 3: Compounds of the formula I.C, in which L and $R^1$ for each individual compound corresponds in each case to one line A-1 to A-72 of Table A (compounds I.C.A-1 to I.C.A-72)

TABLE A

| No. | L | $R^1$ |
| --- | --- | --- |
| A-1 | —C(=O)NH— | $CH_3$ |
| A-2 | —C(=O)NH— | $CH_2CH_3$ |
| A-3 | —C(=O)NH— | $CH(CH_3)_2$ |
| A-4 | —C(=O)NH— | $C(CH_3)_3$ |
| A-5 | —C(=O)NH— | cyclopropyl |
| A-6 | —C(=O)NH— | $CH_2$-cyclopropyl |
| A-7 | —C(=O)NH— | $CH_2CH_2CH_2CH_3$ |
| A-8 | —C(=O)NH— | $CH(CH_3)CH_2CH_3$ |
| A-9 | —C(=O)NH— | $CH_2CH(CH_3)CH_3$ |
| A-10 | —C(=O)NH— | allyl |
| A-11 | —C(=O)NH— | propargyl |
| A-12 | —C(=O)NH— | $CH_2$—CN |
| A-13 | —C(=O)NCH$_3$— | $CH_3$ |
| A-14 | —C(=O)NCH$_3$— | $CH_2CH_3$ |
| A-15 | —C(=O)NCH$_3$— | $CH(CH_3)_2$ |
| A-16 | —C(=O)NCH$_3$— | $C(CH_3)_3$ |
| A-17 | —C(=O)NCH$_3$— | cyclopropyl |
| A-18 | —C(=O)NCH$_3$— | $CH_2$-cyclopropyl |
| A-19 | —C(=O)NCH$_3$— | $CH_2CH_2CH_2CH_3$ |
| A-20 | —C(=O)NCH$_3$— | $CH(CH_3)CH_2CH_3$ |
| A-21 | —C(=O)NCH$_3$— | $CH_2CH(CH_3)CH_3$ |
| A-22 | —C(=O)NCH$_3$— | allyl |
| A-23 | —C(=O)NCH$_3$— | propargyl |
| A-24 | —C(=O)NCH$_3$— | $CH_2$—CN |
| A-25 | —S(=O)— | $CH_3$ |
| A-26 | —S(=O)— | $CH_2CH_3$ |
| A-27 | —S(=O)— | $CH(CH_3)_2$ |
| A-28 | —S(=O)— | $C(CH_3)_3$ |
| A-29 | —S(=O)— | cyclopropyl |
| A-30 | —S(=O)— | $CH_2$-cyclopropyl |
| A-31 | —S(=O)— | $CH_2CH_2CH_2CH_3$ |
| A-32 | —S(=O)— | $CH(CH_3)CH_2CH_3$ |
| A-33 | —S(=O)— | $CH_2CH(CH_3)CH_3$ |
| A-34 | —S(=O)— | allyl |
| A-35 | —S(=O)— | propargyl |
| A-36 | —S(=O)— | $CH_2$—CN |
| A-37 | —S(=O)$_2$— | $CH_3$ |
| A-38 | —S(=O)$_2$— | $CH_2CH_3$ |
| A-39 | —S(=O)$_2$— | $CH(CH_3)_2$ |
| A-40 | —S(=O)$_2$— | $C(CH_3)_3$ |
| A-41 | —S(=O)$_2$— | cyclopropyl |
| A-42 | —S(=O)$_2$— | $CH_2$-cyclopropyl |
| A-43 | —S(=O)$_2$— | $CH_2CH_2CH_2CH_3$ |
| A-44 | —S(=O)$_2$— | $CH(CH_3)CH_2CH_3$ |
| A-45 | —S(=O)$_2$— | $CH_2CH(CH_3)CH_3$ |
| A-46 | —S(=O)$_2$— | allyl |
| A-47 | —S(=O)$_2$— | propargyl |
| A-48 | —S(=O)$_2$— | $CH_2$—CN |
| A-49 | —C(=O)— | $CH_3$ |
| A-50 | —C(=O)— | $CH_2CH_3$ |
| A-51 | —C(=O)— | $CH(CH_3)_2$ |
| A-52 | —C(=O)— | $C(CH_3)_3$ |
| A-53 | —C(=O)— | cyclopropyl |
| A-54 | —C(=O)— | $CH_2$-cyclopropyl |
| A-55 | —C(=O)— | $CH_2CH_2CH_2CH_3$ |
| A-56 | —C(=O)— | $CH(CH_3)CH_2CH_3$ |
| A-57 | —C(=O)— | $CH_2CH(CH_3)CH_3$ |
| A-58 | —C(=O)— | allyl |
| A-59 | —C(=O)— | propargyl |
| A-60 | —C(=O)— | $CH_2$—CN |
| A-61 | —C(=S)— | $CH_3$ |
| A-62 | —C(=S)— | $CH_2CH_3$ |
| A-63 | —C(=S)— | $CH(CH_3)_2$ |
| A-64 | —C(=S)— | $C(CH_3)_3$ |
| A-65 | —C(=S)— | cyclopropyl |
| A-66 | —C(=S)— | $CH_2$-cyclopropyl |
| A-67 | —C(=S)— | $CH_2CH_2CH_2CH_3$ |
| A-68 | —C(=S)— | $CH(CH_3)CH_2CH_3$ |
| A-69 | —C(=S)— | $CH_2CH(CH_3)CH_3$ |
| A-70 | —C(=S)— | allyl |
| A-71 | —C(=S)— | propargyl |
| A-72 | —C(=S)— | $CH_2$—CN |

It is understood that when in aqueous media, the compounds of formula I according to the invention may be present in a reversible equilibrium with the corresponding covalently hydrated forms at the CF$_3$-oxadiazole motif (i.e., the compounds of formula I-I and formula I-II as shown below). This dynamic equilibrium may be important for the biological activity of the compounds of the formula I. The designations of $R^1$, $R^2$, L, p, A, W, $R^4$, n and $R^W$ with reference to the compounds of formula I of the present invention apply generally to the compounds of Formula I-I and Formula I-II, as do the specific disclosures for the individual compounds disclosed in Tables 1 to 3, or the individual compounds disclosed in Tables C.1, C.2 and C.3 below.

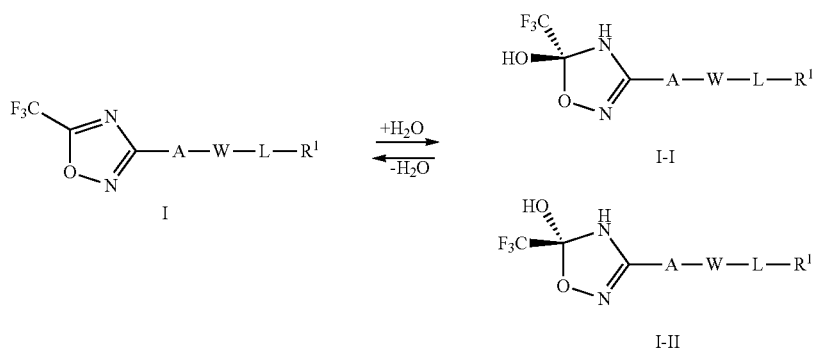

Compounds of the present invention can be made as shown in the following schemes, in which, unless otherwise stated, the definition of each variable is as defined above for a compound of formula I.

The compounds of the formula I can be prepared according to methods or in analogy to methods that are described in the prior art. The synthesis takes advantage of starting materials that are commercially available or may be prepared according to conventional procedures starting from readily available compounds.

For example, compounds of the formula I can be prepared by reacting a compound of the formula II, wherein the nitrogen atom in group W is unsubstituted, with compounds of type III, for example with a carboxylic acid chloride or anhydride, wherein LG is chlorine or carboxylate, in an organic solvent and in the presence of a base. Alternatively compound I can be obtained by reacting of compound II with the corresponding acid III, wherein LG is OH, using peptide coupling reaction conditions such as EDCI and HOBt (for precedents see for example Bioorganic & Medicinal Chemistry Letters, 20(15), 4550-4554; 2010).

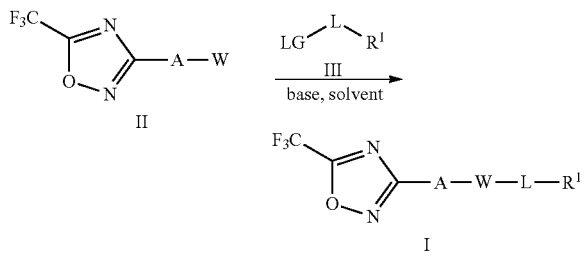

In one aspect the invention relates to a process for preparing compounds of the formula I, which comprises the process step of reacting a compound of the formula II with compounds of type III as described above, to give compounds of the formula I, and wherein the variables A, $R^A$, W and $R^W$ are as defined or preferably defined herein for compounds of the formula I. Another embodiment of the invention relates to intermediate compounds of the formula II, wherein the variables A, $R^A$, W and $R^W$ are as defined or preferably defined herein for compounds of the formula I.

In one aspect the invention relates to intermediate compounds of the formula II.a

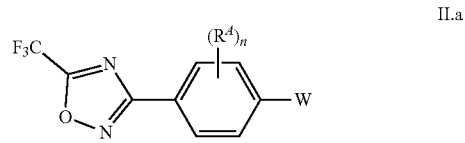

wherein the variables n, $R^A$, W and $R^W$ are as defined or preferably defined herein for compounds of the formula I; and wherein the nitrogen atom in group W is unsubstituted (the nitrogen atom carries one hydrogen).

In a further embodiment the invention relates to intermediate compounds of the formulae II.a1, II.a2 and II.a3

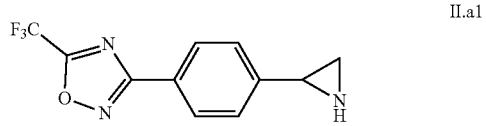

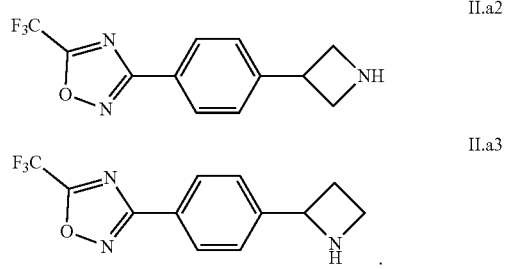

Compounds II, wherein the nitrogen atom in group W is unsubstituted, can be prepared from compounds of the formula IV, wherein the nitrogen atom in group W is protected by a suitable protecting group PG, for example, tert-butyloxycarbonyl. This may be achieved using acidic conditions (e.g. 3 M hydrochloric acid) at temperatures between 0° C. and 100° C., in a suitable solvent.

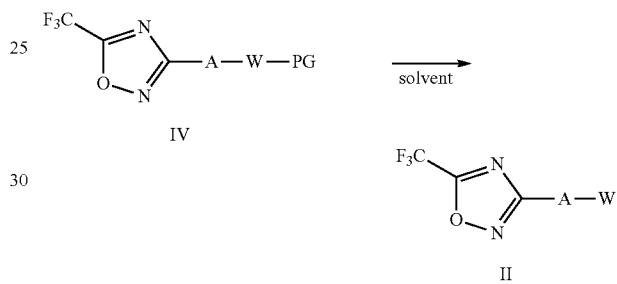

Compounds of the formula IV can be prepared by reacting amidines of type V with trifluoroacetic anhydride in an organic solvent, preferably an ethereal solvent at temperatures between 0° C. and 100° C., preferably at room temperature, as previously described in WO2013/008162.

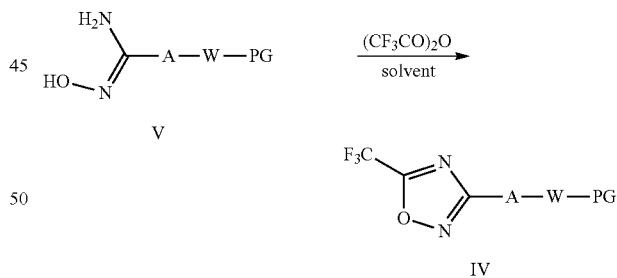

A skilled person will recognize that compounds of type V can be accessed by treating nitriles of type VI with hydroxylamine or its hydrochloride salt in an organic solvent, such as methanol, at a temperature between 0° C. and 100° C. and in the presence of a base such as sodium carbonate (for precedents see for example WO2009/074950, WO2006/013104, EP1932843).

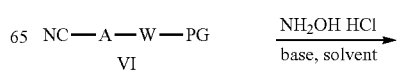

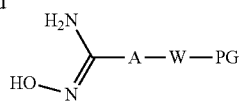

V

Compounds of the formula VI, wherein W is a 4-membered non-aromatic heterocycle containing as ring member atoms besides carbon atoms 1 nitrogen atom, can be prepared by transition metal catalyzed coupling, which involves treating boronic acids of type VII with a compound of type VIII, wherein X is bromine or iodine. For precedents see for example WO 2013/053690, WO 2013/053690, WO 2015/095767.

NC—A—B(OH)$_2$ $\quad\xrightarrow{\text{X—W—PG}\atop\text{VIII}}\quad$ NC—A—W—PG VII $\qquad\qquad\qquad\qquad$ VI Compounds of the formula II, wherein W is a 3-membered non-aromatic heterocycle containing as ring member atoms besides carbon atoms 1 nitrogen atom, can be prepared by epoxidation of the respective olefin of the formula XII and subsequent replacement of the oxygen by nitrogen using sodium azide and triphenylphosphine. Therefore, treating compounds of formula II with an oxidizing agent such as meta-chloroperoxybenzoic acid or tert-butyl hydroperoxide yields an oxirane (Journal of the American Chemical Society, 138(16), 5230-5233, 2016; European Journal of Organic Chemistry, (16), 2767-2773, 2008). This oxirane is then converted to the aziridine using sodium azide and triphenylphosphine as described in Journal of Organic Chemistry, 72(5), 2007, 1737-1741; Organic Letters, 12(17), 2010, 3772-3775.

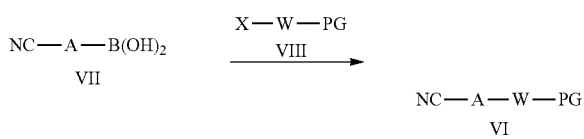

Compounds of the formula XII can be prepared by reacting amidines of type XIII in analogy to the procedure described above for the transformation of compound V to compound IV.

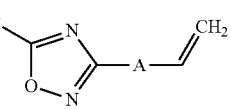

XII

A skilled person will recognize that compounds of type XIII can be accessed by treating nitriles of type XIV in analogy to the procedure described above for the transformation of compound VI to compound V.

Alternatively, compounds of formula I can be prepared from compounds of formula XV in analogy to the procedure described above for the transformation of compound V to compound IV.

In one aspect the invention relates to a process for preparing compounds of the formula I, which comprises the process step of reacting a compound of the formula XV with trifluoroacetic anhydride, to give compounds of the formula I, and wherein the variables A, $R^A$, W, $R^W$, L, p, $R^1$ and $R^2$ are as defined or preferably defined herein for compounds of the formula I. Another embodiment of the invention relates to intermediate compounds of the formula XV, wherein the variables A, $R^A$, W, $R^W$, L, p, $R^1$ and $R^2$ are as defined or preferably defined herein for compounds of the formula I.

In one aspect the invention relates to intermediate compounds of the formula XV.a XV.a wherein the variables $R^A$, n, W, $R^W$, L, p, $R^1$ and $R^2$ are as defined or preferably defined herein for compounds of the formula I.

In a further embodiment the invention relates to intermediate compounds of the formulae XV.a1, XV.a2 and XV.a3,

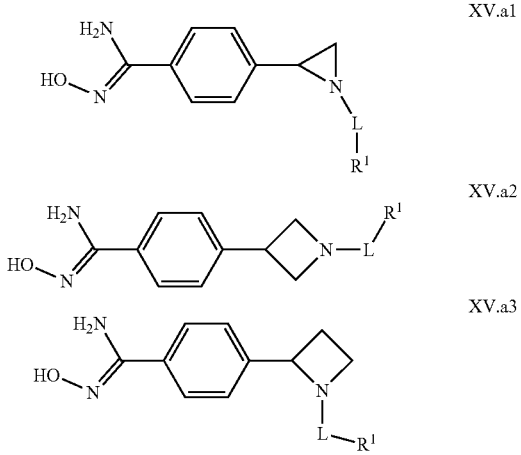

wherein L, p, $R^1$ and $R^2$ are as defined or preferably defined herein for compounds of the formula I.

Preferably the group L in compounds of the formulae XV, XV.a, XV.a1, XV.a2 and XV.a3 is —C(=O)—, —S(=O)$_2$— or —C(=O)NH—.

In a further embodiment the invention relates to intermediate compounds of the formula XV.1a, wherein L is —C(=O)—, —S(=O)$_2$— or —C(=O)NH—; and wherein $R^1$ is hydrogen, $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_3$-$C_8$-cycloalkyl, $C_3$-$C_8$-cycloalkenyl, $C_3$-$C_8$-cycloalkyl-$C_1$-$C_4$-alkyl, phenyl-$C_1$-$C_4$-alkyl, heteroaryl-$C_1$-$C_4$-alkyl-, phenyl, or a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein the heteroaryl group in heteroaryl-$C_1$-$C_4$-alkyl is a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein any of the aliphatic or cyclic groups $R^1$ are unsubstituted or substituted with 1, 2, 3 or up to the maximum possible number of identical or different radicals selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

In a further embodiment the invention relates to intermediate compounds of the formula XV.1a, wherein L is —C(=O)—, —S(=O)$_2$— or —C(=O)NH—; and wherein $R^1$ is hydrogen, $C_1$-$C_6$-alkyl, $C_2$-$C_6$-alkenyl, $C_3$-$C_6$-alkynyl or $C_3$-$C_{11}$-cycloalkyl.

In a further embodiment the invention relates to intermediate compounds of the formula XV.1a, wherein L is —C(=O)—, —S(=O)$_2$— or —C(=O)NH—; and wherein $R^1$ is hydrogen, methyl, ethyl, n-propyl, iso-propyl, n-butyl, iso-butyl, sec-butyl, tert-butyl or cyclopropyl.

In a further embodiment the invention relates to intermediate compounds of the formula XV.2a, wherein L is —C(=O)—, —S(=O)$_2$— or —C(=O)NH—; and wherein $R^1$ is hydrogen, $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_3$-$C_8$-cycloalkyl, $C_3$-$C_8$-cycloalkenyl, $C_3$-$C_8$-cycloalkyl-$C_1$-$C_4$-alkyl, phenyl-$C_1$-$C_4$-alkyl, heteroaryl-$C_1$-$C_4$-alkyl-, phenyl, or a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein the heteroaryl group in heteroaryl-$C_1$-$C_4$-alkyl is a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein any of the aliphatic or cyclic groups $R^1$ are unsubstituted or substituted with 1, 2, 3 or up to the maximum possible number of identical or different radicals selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

In a further embodiment the invention relates to intermediate compounds of the formula XV.2a, wherein L is —C(=O)—, —S(=O)$_2$— or —C(=O)NH—; and wherein $R^1$ is hydrogen, $C_1$-$C_6$-alkyl, $C_2$-$C_6$-alkenyl, $C_3$-$C_6$-alkynyl or $C_3$-$C_{11}$-cycloalkyl.

In a further embodiment the invention relates to intermediate compounds of the formula XV.2a, wherein L is —C(=O)—, —S(=O)$_2$— or —C(=O)NH—; and wherein $R^1$ is hydrogen, methyl, ethyl, n-propyl, iso-propyl, n-butyl, iso-butyl, sec-butyl, tert-butyl or cyclopropyl.

In a further embodiment the invention relates to intermediate compounds of the formula XV.3a, wherein L is —C(=O)—, —S(=O)$_2$— or —C(=O)NH—; and wherein $R^1$ is hydrogen, $C_1$-$C_6$-alkyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_3$-$C_8$-cycloalkyl, $C_3$-$C_8$-cycloalkenyl, $C_3$-$C_8$-cycloalkyl-$C_1$-$C_4$-alkyl, phenyl-$C_1$-$C_4$-alkyl, heteroaryl-$C_1$-$C_4$-alkyl-, phenyl, or a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein the heteroaryl group in heteroaryl-$C_1$-$C_4$-alkyl is a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein any of the aliphatic or cyclic groups $R^1$ are unsubstituted or substituted with 1, 2, 3 or up to the maximum possible number of identical or different radicals selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy and $C_3$-$C_8$-cycloalkyl.

In a further embodiment the invention relates to intermediate compounds of the formula XV.3a, wherein L is —C(=O)—, —S(=O)$_2$— or —C(=O)NH—; and wherein $R^1$ is hydrogen, $C_1$-$C_6$-alkyl, $C_2$-$C_6$-alkenyl, $C_3$-$C_6$-alkynyl or $C_3$-$C_{11}$-cycloalkyl.

In a further embodiment the invention relates to intermediate compounds of the formula XV.3a, wherein L is —C(=O)—, —S(=O)$_2$— or —C(=O)NH—; and wherein $R^1$ is hydrogen, methyl, ethyl, n-propyl, iso-propyl, n-butyl, iso-butyl, sec-butyl, tert-butyl or cyclopropyl.

Particularly preferred examples of intermediates are compounds of the formula XV.a1, namely compounds XV.a1.A-1 to XV.a1.A-72, wherein the meaning of the radicals L and R¹ for each individual compound corresponds in each case to one line A-1 to A-72 of Table A. Particularly preferred examples of intermediates are compounds of the formula XV.a2, namely compounds XV.a2.A-1 to XV.a2.A-72, wherein the meaning of the radicals L and R¹ for each individual compound corresponds in each case to one line A-1 to A-72 of Table A. Particularly preferred examples of intermediates are compounds of the formula XV.a3, namely compounds XV.a3.A-1 to XV.a3.A-72, wherein the meaning of the radicals L and R¹ for each individual compound corresponds in each case to one line A-1 to A-72 of Table A.

Compounds of the formula XV can be prepared from compounds of the formula XVI in analogy to the procedure described above for the transformation of compound VI to compound V.

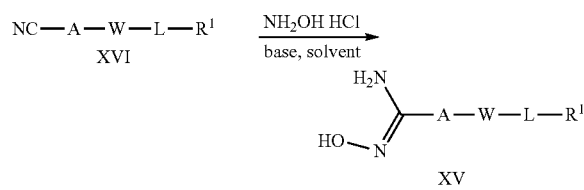

Compounds of the formula XVI can be prepared by reacting compounds of type XVII in analogy to the procedure described above for the transformation of compound II to compound I.

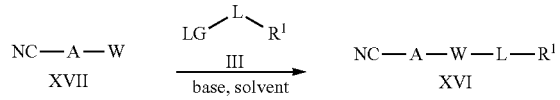

Compounds of the formula XVII can be prepared from compounds of the formula VI in analogy to the procedure described above for the transformation of compound IV to compound II.

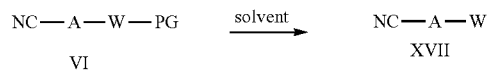

Compounds XVII, can be prepared from compounds of the formula XVIII in analogy to the procedure described above for the transformation of compound XII to compound or the procedure described for the transformation of compound VII to compound VI.

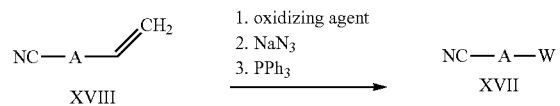

Compounds of the formula VII, XIV and XVIII are commercially available.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, to create mutations at a specific locus of a plant genome. Targeted mutagenesis techniques frequently use oligonucleotides or proteins like CRISPR/Cas, zinc-finger nucleases, TALENs or meganucleases to achieve the targeting effect. Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by mutagenesis and breeding comprise plant varieties commercially available under the name Clearfield®.

Herbicide tolerance has been created via the use of transgenes to glyphosate, glufosinate, 2,4-D, dicamba, oxynil herbicides, like bromoxynil and ioxynil, sulfonylurea herbicides, ALS inhibitors and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621, goxv247; for tolerance to glufosinate: pat and bar, for tolerance to 2,4-D: aad-1, aad-12; for tolerance to dicamba: dmo; for tolerance to oxynil herbicies: bxn; for tolerance to sulfonylurea herbicides: zm-hra, csr1-2, gm-hra, S4-HrA; for tolerance to ALS inhibitors: csr1-2; and for tolerance to HPPD inhibitors: hppdPF, W336, avhppd-03.

Transgenic corn events comprising herbicide tolerance genes include, but are not limited to, DAS40278, MON801, MON802, MON809, MON810, MON832, MON87411, MON87419, MON87427, MON88017, MON89034, NK603, GA21, MZHG0JG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes include, but are not limited to, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes include, but are not limited to, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants: Transgenes which have most frequently been used are toxin genes of *Bacillus* spp. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin, such as genes coding for protease inhibitors, like CpTI and pinII, have been transferred to other plants. A further approach uses transgenes such as dvsnf7 to produce double-stranded RNA in plants.

Transgenic corn events comprising genes for insecticidal proteins or double stranded RNA include, but are not limited to, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098. Transgenic soybean events comprising genes for insecticidal proteins include, but are not limited to, MON87701, MON87751 and DAS-81419. Transgenic cotton events comprising genes for insecticidal proteins include, but are not limited to, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by using the transgene athb17, being present for example in corn event MON87403, or by using the transgene bbx32, being present for example in the soybean event MON87712.

Cultivated plants comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, such as drought, has been created by using the transgene cspB, comprised by the corn event MON87460 and by using the transgene Hahb-4, comprised by soybean event IND-ØØ41Ø-5.

Traits are frequently combined by combining genes in a transformation event or by combining different events during the breeding process resulting in a cultivated plant with stacked traits. Preferred combinations of traits are combinations of herbicide tolerance traits to different groups of herbicides, combinations of insect tolerance to different kind of insects, in particular tolerance to lepidopteran and coleopteran insects, combinations of herbicide tolerance with one or several types of insect resistance, combinations of herbicide tolerance with increased yield as well as combinations of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" (http://www.isaaa.org/gmapprovaldatabase) and the "Center for Environmental Risk Assessment (CERA)" (http://cera-gmc.org/GMCropDatabase). Further information on specific events and methods to detect them can be found for canola events MS1, MS8, RF3, GT73, MON88302, KK179 in WO01/031042, WO01/041558, WO01/041558, WO02/036831, WO11/153186, WO13/003558, for cotton events MON1445, MON15985, MON531 (MON15985), LLCotton25, MON88913, COT102, 281-24-236, 3006-210-23, COT67B, GHB614, T304-40, GHB119, MON88701, 81910 in WO02/034946, WO02/100163, WO02/100163, WO03/013224, WO04/072235, WO04/039986, WO05/103266, WO05/103266, WO06/128573, WO07/017186, WO08/122406, WO08/151780, WO12/134808, WO13/112527; for corn events GA21, MON810, DLL25, TC1507, MON863, MIR604, LY038, MON88017, 3272, 59122, NK603, MIR162, MON89034, 98140, 32138, MON87460, 5307, 4114, MON87427, DAS40278, MON87411, 33121, MON87403, MON87419 in WO98/044140, US02/102582, US03/126634, WO04/099447, WO04/011601, WO05/103301, WO05/061720, WO05/059103, WO06/098952, WO06/039376, US2007/292854, WO07/142840, WO07/140256, WO08/112019, WO09/103049, WO09/111263, WO10/077816, WO11/084621, WO11/062904, WO11/022469, WO13/169923, WO14/116854, WO15/053998, WO15/142571; for potato events E12, F10, J3, J55, V11, X17, Y9 in WO14/178910, WO14/178913, WO14/178941, WO14/179276, WO16/183445, WO17/062831, WO17/062825; for rice events LLRICE06, LLRICE601, LLRICE62 in WO00/026345, WO00/026356, WO00/

026345; and for soybean events H7-1, MON89788, A2704-12, A5547-127, DP305423, DP356043, MON87701, MON87769, CV127, MON87705, DAS68416-4, MON87708, MON87712, SYHT0H2, DAS81419, DAS81419 x DAS44406-6, MON87751 in WO04/074492, WO06/130436, WO06/108674, WO06/108675, WO08/054747, WO08/002872, WO09/064652, WO09/102873, WO10/080829, WO10/037016, WO11/066384, WO11/034704, WO12/051199, WO12/082548, WO13/016527, WO13/016516, WO14/201235.

The use of compounds I and compositions according to the invention, respectively, on cultivated plants may result in effects which are specific to a cultivated plant comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, *Mycoplasma*, viral or viroid pathogens as well as early vigour, early or delayed ripening, cold or heat tolerance as well as changed amino acid or fatty acid spectrum or content.

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables (e.g. *A. dauci* or *A. porri*), oilseed rape (*A. brassicicola* or *brassicae*), sugar beets (*A. tenuis*), fruits (e.g. *A. grandis*), rice, soybeans, potatoes and tomatoes (e. g. *A. solani*, *A. grandis* or *A. alternata*), tomatoes (e. g. *A. solani* or *A. alternata*) and wheat (e.g. *A. triticina*); *Aphanomyces* spp. on sugar beets and vegetables; *Ascochyta* spp. on cereals and vegetables, e. g. *A. tritici* (anthracnose) on wheat and *A. hordei* on barley; *Aureobasidium zeae* (syn. *Kapatiella zeae*) on corn; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuceliana*: grey mold) on fruits and berries (e. g. strawberries), vegetables (e. g. lettuce, carrots, celery and cabbages); *B. squamosa* or *B. allii* on onion family), oilseed rape, ornamentals (e.g. *B eliptica*), vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladobotryum* (syn. *Dactylium*) spp. (e.g. *C. mycophilum* (formerly *Dactylium dendroides*, teleomorph: *Nectria albertinii*, *Nectria rosella* syn. *Hypomyces rosellus*) on mushrooms; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*), soybeans (e. g. *C. truncatum* or *C. gloeosporioides*), vegetables (e.g. *C. lagenarium* or *C. capsici*), fruits (e.g. *C. acutatum*), coffee (e.g. *C. coffeanum* or *C. kahawae*) and *C. gloeosporioides* on various crops; *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; *esca* (dieback, apoplexy) on vines, caused by *Formitiporia* (syn. *Phellinus*) *punctata*, *F. mediterra*, *Phaeomoniella chlamydospora* (formerly *Phaeoacremonium chlamydosporum*), *Phaeoacremonium aleophllum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, oilseed rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals, potatoes and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monllinia* spp., e. g. *M. laxa*, *M. fructicola* and *M. fructigena* (syn. *Monilia* spp.: bloom and twig blight, brown rot) on stone fruits and other rosaceous plants; *Mycosphaerella* spp. on cereals, bananas, soft fruits and ground nuts, such as e. g. *M. graminicola* (anamorph: *Zymoseptoria tritici* formerly *Septoria tritici*: Septoria blotch) on wheat or *M. fijiensis* (syn. *Pseudocercospora fijiensis*: black Sigatoka disease) and *M. musicola* on bananas, *M. arachidicola* (syn. *M. arachidis* or *Cercospora arachidis*), *M. berkeleyi* on peanuts, *M. pisi* on peas and *M. brasiciola* on brassicas; *Peronospora* spp. (downy mildew) on cabbage (e. g. *P. brassicae*), oilseed rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (syn. *Leptosphaeria biglobosa* and *L. maculans*: root and stem rot) on oilseed rape and cabbage, *P. betae* (root rot, leaf spot and damping-off) on sugar beets and *P. zeaemaydis* (syn. *Phyllostica zeae*) on corn; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, oilseed rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits (e. g. *P. leucotricha* on apples) and curcurbits (*P. xanthii*); *Polymyxa* spp., e. g. on cereals, such as barley and wheat (*P. graminis*) and sugar beets (*P. betae*) and thereby transmitted viral diseases; *Pseudocercosporella herpotrichoides* (syn. *Oculimacula yallundae, O. acuformis*: eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenopeziza* spp., e.g. *P. brassicae* on oilseed rape; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*: rice blast) on rice and *P. grisea* on turf and cereals; *Pythium* spp. (damping-off) on turf, rice, corn, wheat, cotton, oilseed rape, sunflowers, soybeans, sugar beets, vegetables and various other plants (e. g. *P. ultimum* or *P. aphanidermatum*) and *P. oligandrum* on mushrooms; *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, oilseed rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* and *R. commune* (scald) on barley, rye and triticale; *Sarocladium oryzae* and *S. attenuatum* (sheath rot) on rice; *Sclerotinia* spp. (stem rot or white mold) on vegetables (*S. minor* and *S. sclerotiorum*) and field crops, such as oilseed rape, sunflowers (e. g. *S. sclerotiorum*) and soybeans, *S. rolfsii* (syn. *Athelia rolfsii*) on soybeans, peanut, vegetables, corn, cereals and ornamentals; *Septoria* spp. on various plants, e. g. *S. glycines* (brown spot) on soybeans, *S. tritici* (syn. *Zymoseptoria tritici, Septoria* blotch) on wheat and S. (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setosphaeria* spp. (leaf blight) on corn (e. g. *S. turcicum*, syn. *Helminthosporium turcicum*) and turf; *Sphacelotheca* spp. (smut) on corn, (e. g. *S. reiliana*, syn. *Ustilago reiliana*: head smut), sorghum and sugar cane; *Sphaerotheca fuliginea* (syn. *Podosphaera xanthii*: powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*, syn. *Septoria nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Trichoderma harzianum* on mushrooms, *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*), sugar beets (e. g. *U. betae* or *U. beticola*) and on pulses (e.g. *U. vignae, U. pisi, U. viciae-fabae* and *U. fabae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. longisporum* on oilseed rape, *V. dahliae* on strawberries, oilseed rape, potatoes and tomatoes, and *V. fungicola* on mushrooms; *Zymoseptoria tritici* on cereals.

In a preferred embodiment the compounds I, their mixtures with other active compounds as defined herein and compositions thereof, respectively, are particularly suitable for controlling the following plant diseases: *Puccinia* spp. (rusts) on various plants, for example, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. sorghi* (common rust) on maize, *P. polysora* (southern rust) on maize; *P. coronata* e.g. on oats, *P. sorghi* and *P. polysora* on corn; *Puccinia* spp. on other crops, e.g. *P. heliathi* on sunflower, *P. arachidis* on peanuts; *Uromyces* spp. on pulses and other crops crops, e.g. *Uromyces viciae-fabae, Uromyces vigniae, Uromyces pisi, U. cicerisarietini, U. betae* syn *U. beticola*; and *Phakopsoraceae* spp. on various plants, in particular *Phakopsora pachyrhizi* and *P. meibomiae* (soybean rust) on soybeans.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecllomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi. Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-soluble concentrates (SL, LS)

10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible concentrates (DC)

5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable concentrates (EC)

15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-dispersible granules and water-soluble granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-low volume liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration Inhibitors

Inhibitors of complex III at $Q_o$ site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylidene-aminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21a), methyl-N-[2-[(1,4-dimethyl-5-phenyl-pyrazol-3-yl)oxylmethyl]phenyl]-N-methoxy-carbamate (A.1.22), metyltetrapole (A.1.25), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxymethylen)phenyl)-3-methoxy-acrylic acid methylester (A.1.38);

inhibitors of complex III at $Q_i$ site: cyazofamid (A.2.1), amisulbrom (A.2.2), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A.2.3), fenpicoxamid (A.2.4), florylpicoxamid (A.2.5);

inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), inpyrfluxam (A.3.22), pyrapropoyne (A.3.23), fluindapyr (A.3.28), N-[2-[2-chloro-4-(trifluoro-methyl)phenoxy]phenyl]-3-(difluoromethyl)-5-fluoro-1-methyl-pyrazole-4-carboxamide (A.3.29), methyl (E)-2-[2[(5-cyano-2-methyl-phenoxy)methyl]phenyl]-3-methoxy-prop-2-enoate (A.3.30), isoflucypram (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethylindan-4-yl]pyridine-3-carboxamide (A.3.33), 2-(difluoromethyl)-N-(3-ethyl-1,1-dimethyl-indan-4-yl)pyridine-3-carboxamide (A.3.34), 2-(difluoromethyl)-N-[(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan-4-yl]pyridine-3-carboxamide (A.3.39);

other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e. g. fentin-acetate (A.4.8), fentin chloride (A.4.9) or fentin hydroxide (A.4.10); ametoctradin (A.4.11); silthiofam (A.4.12);

B) Sterol Biosynthesis Inhibitors (SBI Fungicides)
C14 demethylase inhibitors: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 2-(2,4-difluorophenyl)-1,1-difluoro-3-(tetrazol-1-yl)-1-[5-[4-(2,2,2-trifluoroethoxy)phenyl]-2-pyridyl]propan-2-ol (B.1.31), 2-(2,4-difluorophenyl)-1,1-difluoro-3-(tetrazol-1-yl)-1-[5-[4-(trifluoromethoxy)phenyl]-2-pyridyl]propan-2-ol (B.1.32), ipfentrifluconazole (B.1.37), mefentrifluconazole (B.1.38), 2-(chloromethyl)-2-methyl-5-(p-tolylmethyl)-1-(1,2,4-triazol-1-ylmethyl) cyclopentanol (B.1.43); imidazoles: imazalil (B.1.44), pefurazoate (B.1.45), prochloraz (B.1.46), triflumizol (B.1.47); pyrimidines, pyridines, piperazines: fenarimol (B.1.49), pyrifenox (B.1.50), triforine (B.1.51), [3-(4-chloro-2-fluorophenyl)-5-(2,4-difluorophenyp-isoxazol-4-yl]-(3-pyridyl)methanol (B.1.52);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);
Other Sterol biosynthesis inhibitors: chlorphenomizole (B.4.1);

C) Nucleic Acid Synthesis Inhibitors
phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8);

D) Inhibitors of Cell Division and Cytoskeleton
tubulin inhibitors: benomyl (D.1.1), carbendazim (D.1.2), fuberidazole (D1.3), thiabendazole (D.1.4), thiophanate-methyl (D.1.5), pyridachlometyl (D.1.6), N-ethyl-2-[(3-ethynyl-8-methyl-6-quinolyl)oxy]butanamide (D.1.8), N-ethyl-2-[(3-ethynyl-8-methyl-6-quinolyl)oxy]-2-methylsulfanyl-acetamide (D.1.9), 2-[(3-ethynyl-8-methyl-6-quinolyl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl-6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3-amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7);

E) Inhibitors of Amino Acid and Protein Synthesis methionine synthesis inhibitors: cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6);

F) Signal Transduction Inhibitors

MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofosmethyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acides: propamocarb (G.4.1);

inhibitors of oxysterol binding protein: oxathiapiprolin (G.5.1), fluoxapiprolin (G.5.3), 4[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4-[1-[2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl]acetyl]-4-piperidyl]-N-tetralin-1-yl-pyridine-2-carboxamide (G.5.11);

H) Inhibitors with Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorbenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4-cyclopropyl-N-(2,4-dimethoxyphenyl)thiadiazole-5-carboxamide (J.1.10);

K) Unknown Mode of Action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), methasulfocarb (K.1.18), nitrapyrin (K.1.19), nitrothal-isopropyl (K.1.20), tolprocarb (K.1.21), oxin-copper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N-methyl formamidine (K.1.27), N'-(4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyl)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N'-[5-bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2-methyl-4-(3-trimethylsilanyl-propoxy)-phenyl)-N-ethyl-N-methyl formamidine (K.1.35), 2-(4-chlorophenyl)-N-[4-(3,4-dimethoxy-phenyl)-isoxazol-5-yl]-2-prop-2-ynyloxy-acetamide (K.1.36), 3-[5-(4-chlorophenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1-(4,6-dimethoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), ipflufenoquin (K.1.44), quinofumelin (K.1.47), 2-(6-benzyl-2-pyridyl)quinazoline (K.1.50), 2-[6-(3-fluoro-4-methoxy-phenyl)-5-methyl-2-pyridyl]quinazoline (K.1.51), dichlobentiazox (K.1.52), N'-(2,5-dimethyl-4-phenoxy-phenyl)-N-ethyl-N-methyl-formamidine (K.1.53), pyrifenamine (K.1.54);

M) Growth Regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl, uniconazole;

N) Herbicides from Classes N.1 to N.15

N.1 Lipid biosynthesis inhibitors: alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-chloro-4-cyclo¬propyl-2'-fluoro[1,1'-biphenyl]-3-yl)-5-hydroxy-2,2,6,6-tetramethyl-2H-pyran-3(6H)-one (1312337-72-6); 4-(2',4'-dichloro-4-cyclopropyl[1,1'-biphenyl]-3-yl)-5-hydroxy-2,2,6,6-tetramethyl-2H-pyran-3(6H)-one (1312337-45-3); 4-(4'-chloro-4-ethyl-2'-fluoro[1,1'-biphenyl]-3-yl)-5-hydroxy-2,2,6,6-tetramethyl-2H-pyran-3(6H)-one (1033757-93-5); 4-(2',4'-dichloro-4-ethyl[1,1'-biphenyl]-3-yl)-2,2,6,6-tetramethyl-2H-pyran-3,5(4H,6H)-dione (1312340-84-3); 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one (1312337-48-6); 5-(acetyloxy)-4-(2',4'-dichloro-4-cyclopropyl-[1,1'-biphenyl]-3-yl)-3,6-dihydro-2,2,6,6-tetramethyl-2H-pyran-3-one; 5-(acetyloxy)-4-(4'-chloro-4-ethyl-2'-fluoro[1,1'-biphenyl]-3-yl)-3,6-dihydro-2,2,6,6-tetramethyl-2H-pyran-3-one (1312340-82-1); 5-(acetyloxy)-4-(2',4'-dichloro-4-ethyl[1,1'-biphenyl]-3-yl)-3,6-dihydro-2,2,6,6-tetramethyl-2H-pyran-3-one (1033760-55-2); 4-(4'-chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (1312337-51-1); 4-(2',4'-dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (1312340-83-2); 4-(2',4'-dichloro-4-ethyl¬[1,1'-biphenyl]-3-yl)-5,6-dihydro-2,2,6,6-tetramethyl-5-oxo-2H-pyran-3-yl carbonic acid methyl ester (1033760-58-5); benfuresate, butylate, cycloate, dalapon, dimepiperate, EPTC, esprocarb, ethofumesate, flupropanate, molinate, orbencarb, pebulate, prosulfocarb, TCA, thioben-carb, tiocarbazil, triallate, vernolate;

N.2 ALS inhibitors: amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuronmethyl, trifloxysulfuron, triflusulfuron, triflusulfuron-methyl, tritosulfuron, imazamethabenz, imazamethabenz-methyl, imazamox, imazapic, imazapyr, imazaquin, imazethapyr; cloransulam, cloransulam-methyl, diclosulam, flumetsulam, florasulam, metosulam, penoxsulam, pyrimisulfan, pyroxsulam; bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methyhethyl ester (420138-41-6), 4-[[[2-[(4,6-dimethoxy-2-pyrimidinyl)oxy]phenyl]methyl]amino]-benzoic acid propyl ester (420138-40-5), N-(4-bromophenyl)-2-[(4,6-dimethoxy-2-pyrimidinyl)oxy]-benzenemethanamine (420138-01-8); flucarbazone, flucarbazone-sodium, propoxycarbazone, propoxycarbazone-sodium, thiencarbazone, thiencarbazone-methyl; triafamone;

N.3 Photosynthesis inhibitors: amicarbazone; chlorotriazine; ametryn, atrazine, chloridazone, cyanazine, desmetryn, dimethametryn, hexazinone, metribuzin, prometon, prometryn, propazine, simazine, simetryn, terbumeton, terbuthylazin, terbutryn, trietazin; chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron, thiadiazuron, desmedipham, karbutilat, phenmedipham, phenmedipham-ethyl, bromofenoxim, bromoxynil and its salts and esters, ioxynil and its salts and esters, bromacil, lenacil, terbacil, bentazon, bentazon-sodium, pyridate, pyridafol, pentanochlor, propanil; diquat, diquat-dibromide, paraquat, paraquat-dichloride, paraquat-dimetilsulfate;

N.4 protoporphyrinogen-IX oxidase inhibitors: acifluorfen, acifluorfen-sodium, azafenidin, bencarbazone, benzfendizone, bifenox, butafenacil, carfentrazone, carfentrazone-ethyl, chlormethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacetmethyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (353292-31-6), N-ethyl-3-(2,6-dichloro-4-trifluoro-methylphenoxy)-5-methyl-1H-pyrazole-1-carboxamide (452098-92-9), N-tetrahydrofurfuryl-3-(2,6-dichloro-4-trifluoromethylphenoxy)-5-methyl-1H-pyrazole-1-carboxamide (915396-43-9), N-ethyl-3-(2-chloro-6-fluoro-4-trifluoromethyl¬phenoxy)-5-methyl-1H-pyrazole-1-carboxamide (452099-05-7), N-tetrahydro¬furfuryl-3-(2-chloro-6-fluoro-4-trifluoro¬methylphenoxy)-5-methyl-1H-pyrazole-1-carboxamide (452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (1300118-96-0), 1-methyl-6-trifluoro¬methyl-3-(2,2,7-trifluoro-3-oxo-4-prop-2-ynyl-3,4-dihydro-2H-benzo[1,4]oxazin-6-yl)-1H-pyrimidine-2,4-dione (1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (948893-00-3), 3-[7-chloro-5-fluoro-2-(trifluoromethyl)-

1H-benzimidazol-4-yl]-1-methyl-6-(trifluoromethyl)-1H-pyrimidine-2,4-dione (212754-02-4);

N.5 Bleacher herbicides: beflubutamid, diflufenican, fluridone, flurochloridone, flurtamone, norflurazon, picolinafen, 4-(3-trifluoromethyl-phenoxy)-2-(4-trifluoromethylphenyl)pyrimidine (180608-33-7); benzobicyclon, benzofenap, bicyclopyrone, clomazone, fenquintrione, isoxaflutole, mesotrione, pyrasulfotole, pyrazolynate, pyrazoxyfen, sulcotrione, tefuryltrione, tembotrione, tolpyralate, topramezone; aclonifen, amitrole, flumeturon;

N.6 EPSP synthase inhibitors: glyphosate, glyphosate-isopropylammonium, glyposatepotassium, glyphosate-trimesium (sulfosate);

N.7 Glutamine synthase inhibitors: bilanaphos (bialaphos), bilanaphos-sodium, glufosinate, glufosinate-P, glufosinate-ammonium;

N.8 DHP synthase inhibitors: asulam;

N.9 Mitosis inhibitors: benfluralin, butralin, dinitramine, ethalfluralin, fluchloralin, oryzalin, pendimethalin, prodiamine, trifluralin; amiprophos, amiprophos-methyl, butamiphos; chlorthal, chlorthal-dimethyl, dithiopyr, thiazopyr, propyzamide, tebutam; carbetamide, chlorpropham, flamprop, flamprop-isopropyl, flamprop-methyl, flamprop-M-isopropyl, flamprop-M-methyl, propham;

N.10 VLCFA inhibitors: acetochlor, alachlor, butachlor, dimethachlor, dimethenamid, dimethenamid-P, metazachlor, metolachlor, metolachlor-S, pethoxamid, pretilachlor, propachlor, propisochlor, thenylchlor, flufenacet, mefenacet, diphenamid, naproanilide, napropamide, napropamide-M, fentrazamide, anilofos, cafenstrole, fenoxasulfone, ipfencarbazone, piperophos, pyroxasulfone, isoxazoline compounds of the formulae II.1, II.2, II.3, II.4, II.5, II.6, II.7, II.8 and II.9

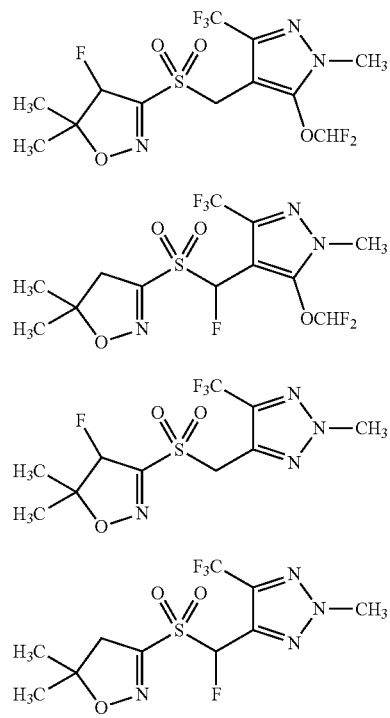

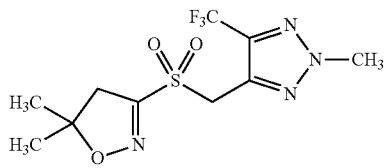

II.5

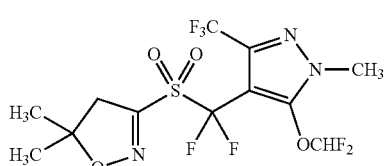

II.6

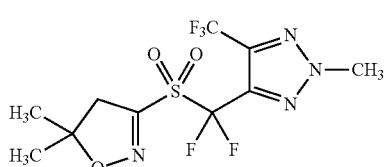

II.7

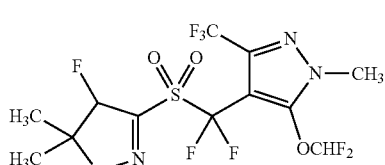

II.8

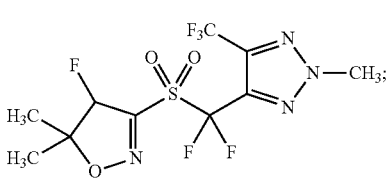

II.9

N.11 Cellulose biosynthesis inhibitors: chlorthiamid, dichlobenil, flupoxam, indaziflam, isoxaben, triaziflam, 1-cyclohexyl-5-pentafluorphenyloxy-14-[1,2,4,6]thiatriazin-3-ylamine (175899-01-1);

N.12 Decoupler herbicides: dinoseb, dinoterb, DNOC and its salts;

N.13 Auxinic herbicides: 2,4-D and its salts and esters, clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid, benzyl 4-amino-3-chloro-6-(4-chloro-2-fluoro-3-methoxyphenyl)-5-fluoropyridine-2-carboxylate (1390661-72-9);

N.14 Auxin transport inhibitors: diflufenzopyr, diflufenzopyr-sodium, naptalam, naptalamsodium;

N.15 Other herbicides: bromobutide, chlorflurenol, chlorflurenol-methyl, cinmethylin, cumyluron, cyclopyrimorate (499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (403640-27-7), methyl azide, methyl bromide, methyl-dymron, methyl iodide, MSMA, oleic acid, oxaziclomefone, pelargonic acid, pyributicarb, quinoclamine, tridiphane;

O) Insecticides from Classes O.1 to O.29

O.1 Acetylcholine esterase (AChE) inhibitors: aldicarb (O.1.1), alanycarb (O.1.2), bendiocarb (O.1.3), benfuracarb (O.1.4), butocarboxim (O.1.5), butoxycarboxim (O.1.6), carbaryl (O.1.7), carbofuran (O.1.8), carbosulfan (O.1.9), ethiofencarb (O.1.10), fenobucarb (O.1.11), formetanate (O.1.12), furathiocarb (O.1.13), isoprocarb (O.1.14), methiocarb (O.1.15), methomyl (O.1.16), metolcarb (O.1.17), oxamyl (O.1.18), pirimicarb (O.1.19), propoxur (O.1.20), thiodicarb (O.1.21), thiofanox (O.1.22), trimethacarb (O.1.23), XMC (O.1.24), xylylcarb (O.1.25), triazamate (O.1.26), acephate (O.1.27), azamethiphos (O.1.28), azinphos-ethyl (O.1.29), azinphosmethyl (O.1.30), cadusafos (O.1.31), chlor-ethoxyfos (O.1.32), chlorfenvinphos (O.1.33), chlormephos (O.1.34), chlorpyrifos (O.1.35), chlorpyrifos-methyl (O.1.36), coumaphos (O.1.37), cyanophos (O.1.38), demeton-S-methyl (O.1.39), diazinon (O.1.40), dichlorvos/DDVP (O.1.41), dicrotophos (O.1.42), dimethoate (O.1.43), dimethylvinphos (O.1.44), disulfoton (O.1.45), EPN (O.1.46), ethion (O.1.47), ethoprophos (O.1.48), famphur (O.1.49), fenamiphos (O.1.50), fenitrothion (O.1.51), fenthion (O.1.52), fosthiazate (O.1.53), heptenophos (O.1.54), imicyafos (O.1.55), isofenphos (O.1.56), isopropyl O-(methoxyaminothio-phosphoryl) salicylate (O.1.57), isoxathion (O.1.58), malathion (O.1.59), mecarbam (O.1.60), methamidophos (O.1.61), methidathion (O.1.62), mevinphos (O.1.63), monocrotophos (O.1.64), naled (O.1.65), omethoate (O.1.66), oxydemeton-methyl (O.1.67), parathion (O.1.68), parathion-methyl (O.1.69), phenthoate (O.1.70), phorate (O.1.71), phosalone (O.1.72), phosmet (O.1.73), phosphamidon (O.1.74), phoxim (O.1.75), pirimiphos-methyl (O.1.76), profenofos (O.1.77), propetamphos (O.1.78), prothiofos (O.1.79), pyraclofos (O.1.80), pyridaphenthion (O.1.81), quinalphos (O.1.82), sulfotep (O.1.83), tebupirimfos (O.1.84), temephos (O.1.85), terbufos (O.1.86), tetrachlorvinphos (O.1.87), thiometon (O.1.88), triazophos (O.1.89), trichlorfon (O.1.90), vamidothion (O.1.91);

O.2 GABA-gated chloride channel antagonists: endosulfan (O.2.1), chlordane (O.2.2), ethiprole (O.2.3), fipronil (O.2.4), flufiprole (O.2.5), pyrafluprole (O.2.6), pyriprole (O.2.7);

O.3 Sodium channel modulators: acrinathrin (O.3.1), allethrin (O.3.2), d-cis-trans allethrin (O.3.3), d-trans allethrin (O.3.4), bifenthrin (O.3.5), kappa-bifenthrin (O.3.6), bioallethrin (O.3.7), bioallethrin S-cylclopentenyl (O.3.8), bioresmethrin (O.3.9), cycloprothrin (O.3.10), cyfluthrin (O.3.11), beta-cyfluthrin (O.3.12), cyhalothrin (O.3.13), lambda-cyhalothrin (O.3.14), gamma-cyhalothrin (O.3.15), cypermethrin (O.3.16), alpha-cypermethrin (O.3.17), beta-cypermethrin (O.3.18), theta-cypermethrin (O.3.19), zeta-cypermethrin (O.3.20), cyphenothrin (O.3.21), deltamethrin (O.3.22), empenthrin (O.3.23), esfenvalerate (O.3.24), etofenprox (O.3.25), fenpropathrin (O.3.26), fenvalerate (O.3.27), flucythrinate (O.3.28), flumethrin (O.3.29), tau-fluvalinate (O.3.30), halfenprox (O.3.31), heptafluthrin (O.3.32), imiprothrin (O.3.33), meperfluthrin (O.3.34), metofluthrin (O.3.35), momfluorothrin (O.3.36), epsilon-momfluorothrin (O.3.37), permethrin (O.3.38), phenothrin (O.3.39), prallethrin (O.3.40), profluthrin (O.3.41), pyrethrin (pyrethrum) (O.3.42), resmethrin (O.3.43), silafluofen (O.3.44), tefluthrin (O.3.45), kappa-tefluthrin (O.3.46), tetramethylfluthrin (O.3.47), tetramethrin (O.3.48), tralomethrin (O.3.49), trans-fluthrin (O.3.50), DDT (O.3.51), methoxychlor (O.3.52);

O.4 Nicotinic acetylcholine receptor agonists (nAChR): acetamiprid (O.4.1), clothianidin (O.4.2), cycloxaprid (O.4.3), dinotefuran (O.4.4), imidacloprid (O.4.5), nitenpyram (O.4.6), thiacloprid (O.4.7), thiamethoxam (O.4.8), 4,5-dihydro-N-nitro-1-(2-oxiranylmethyl)-1H-imidazol-2-amine (O.4.9), (2E)-1-[(6-chloropyridin-3-yl)methyl]-N'-nitro-2-pentylidene-hydrazinecarboximidamide (O.4.10), 1-[(6-chloropyridin-3-yl)methyl]-7-methyl-8-nitro-5-propoxy-1,2,3,5,6,7-hexahydroimidazo[1,2-a]pyridine (O.4.11), nicotine (O.4.12), sulfoxaflor (O.4.13), flupyradifurone (O.4.14), triflumezopyrim (O.4.15);

O.5 Nicotinic acetylcholine receptor allosteric activators: spinosad (O.5.1), spinetoram (O.5.2);

O.6 Chloride channel activators: abamectin (O.6.1), emamectin benzoate (O.6.2), ivermectin (O.6.3), lepimectin (O.6.4), milbemectin (O.6.5);

O.7 Juvenile hormone mimics: hydroprene (O.7.1), kinoprene (O.7.2), methoprene (O.7.3), fenoxycarb (O.7.4), pyriproxyfen (O.7.5);

O.8 miscellaneous non-specific (multi-site) inhibitors: methyl bromide (O.8.1) and other alkyl halides, chloropicrin (O.8.2), sulfuryl fluoride (O.8.3), borax (O.8.4), tartar emetic (O.8.5);

O.9 Chordotonal organ TRPV channel modulators: pymetrozine (O.9.1), pyrifluquinazon (O.9.2), flonicamid (O.9.3);

O.10 Mite growth inhibitors: clofentezine (O.10.1), hexythiazox (O.10.2), diflovidazin (O.10.3), etoxazole (O.10.4);

O.11 Microbial disruptors of insect midgut membranes: *Bacillus thuringiensis, Bacillus sphaericus* and the insecticidal proteins they produce: *Bacillus thuringiensis* subsp. *Israelensis* (O.11.1), *Bacillus sphaericus* (O.11.2), *Bacillus thuringiensis* subsp. *aizawai* (O.11.3), *Bacillus thuringiensis* subsp. *kurstaki* (O.11.4), *Bacillus thuringiensis* subsp. *tenebrionis* (O.11.5), the Bt crop proteins: Cry1Ab (O.11.6), Cry1Ac (O.11.7), Cry1Fa (O.11.8), Cry2Ab (O.11.9), mCry3A (O.11.10), Cry3Ab (O.11.11), Cry3Bb (O.11.12), Cry34/35Ab1 (O.11.13);

O.12 Inhibitors of mitochondrial ATP synthase: diafenthiuron (O.12.1), azocyclotin (O.12.2), cyhexatin (O.12.3), fenbutatin oxide (O.12.4), propargite (O.12.5), tetradifon (O.12.6);

O.13 Uncouplers of oxidative phosphorylation via disruption of the proton gradient: chlorfenapyr (O.13.1), DNOC (O.13.2), sulfluramid (O.13.3);

O.14 Nicotinic acetylcholine receptor (nAChR) channel blockers: bensultap (O.14.1), cartap hydrochloride (O.14.2), thiocyclam (O.14.3), thiosultap sodium (O.14.4);

O.15 Inhibitors of the chitin biosynthesis type 0: bistrifluron (O.15.1), chlorfluazuron (O.15.2), diflubenzuron (O.15.3), flucycloxuron (O.15.4), flufenoxuron (O.15.5), hexaflumuron (O.15.6), lufenuron (O.15.7), novaluron (O.15.8), noviflumuron (O.15.9), teflubenzuron (O.15.10), triflumuron (O.15.11);

O.16 Inhibitors of the chitin biosynthesis type 1: buprofezin (O.16.1);

O.17 Moulting disruptors: cyromazine (O.17.1);
O.18 Ecdyson receptor agonists: methoxyfenozide (O.18.1), tebufenozide (O.18.2), halofenozide (O.18.3), fufenozide (O.18.4), chromafenozide (O.18.5);
O.19 Octopamin receptor agonists: amitraz (O.19.1);
O.20 Mitochondrial complex III electron transport inhibitors: hydramethylnon (O.20.1), acequinocyl (O.20.2), fluacrypyrim (O.20.3), bifenazate (O.20.4);
O.21 Mitochondrial complex I electron transport inhibitors: fenazaquin (O.21.1), fenpyroximate (O.21.2), pyrimidifen (O.21.3), pyridaben (O.21.4), tebufenpyrad (O.21.5), tolfenpyrad (O.21.6), rotenone (O.21.7);
O.22 Voltage-dependent sodium channel blockers: indoxacarb (O.22.1), metaflumizonev (O.22.2), 2-[2-(4-cyanophenyl)-1-[3-(trifluoromethyl)phenyl]ethylidene]-N-[4-(difluoromethoxy)phenyl]-hydrazinecarboxamide (O.22.3), N-(3-chloro-2-methylphenyl)-2-[(4-chlorophenyl)-[4-[methyl(methylsulfonyl)amino]phenyl]methylene]-hydrazinecarboxamide (O.22.4);
O.23 Inhibitors of the of acetyl CoA carboxylase: spirodiclofen (O.23.1), spiromesifen (O.23.2), spirotetramat (O.23.3), spiropidion (O.23.4);
O.24 Mitochondrial complex IV electron transport inhibitors: aluminium phosphide (O.24.1), calcium phosphide (O.24.2), phosphine (O.24.3), zinc phosphide (O.24.4), cyanide (O.24.5);
O.25 Mitochondrial complex II electron transport inhibitors: cyenopyrafen (O.25.1), cyflumetofen (O.25.2);
O.26 Ryanodine receptor-modulators: flubendiamide (O.26.1), chlorantraniliprole (O.26.2), cyantraniliprole (O.26.3), cyclaniliprole (O.26.4), tetraniliprole (O.26.5), (R)-3-chloro-$N^1$-{2-methyl-4-[1,2,2,2-tetrafluoro-1-(trifluoromethyl)ethyl]phenyl}-$N^2$-(1-methyl-2-methylsulfonylethyl)phthalamide (O.26.6), (S)-3-chloro-$N^1$-{2-methyl-4-[1,2,2,2-tetrafluoro-1-(trifluoromethyl)ethyl]phenyl}-$N^2$-(1-methyl-2-methylsulfonylethyl)phthalamide (O.26.7), methyl-2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (O.26.8), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.26.9), N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide (O.26.10), N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide (O.26.11), N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.26.12), N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide (O.26.13), N-[2-(5-amino-1,3,4-thiadiazol-2-yl)-4-chloro-6-methylphenyl]-3-bromo-1-(3-chloro-2-pyridinyl)-1H-pyrazole-5-carboxamide (O.26.14), 3-chloro-1-(3-chloro-2-pyridinyl)-N-[2,4-dichloro-6-[[(1-cyano-1-methylethyl)amino]carbonyl]phenyl]-1H-pyrazole-5-carboxamide (O.26.15), tetrachlorantraniliprole (O.26.16), N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (O.26.17), cyhalodiamide (O.26.18);
O.27: Chordotonal organ Modulators—undefined target site: flonicamid (O.27.1);
O.28. insecticidal active compounds of unknown or uncertain mode of action: afidopyropen (O.28.1), afoxolaner (O.28.2), azadirachtin (O.28.3), amidoflumet (O.28.4), benzoximate (O.28.5), broflanilide (O.28.6), bromopropylate (O.28.7), chinomethionat (O.28.8), cryolite (O.28.9), dicloromezotiaz (O.28.10), dicofol (O.28.11), flufenerim (O.28.12), flometoquin (O.28.13), fluensulfone (O.28.14), fluhexafon (O.28.15), fluopyram (O.28.16), fluralaner (O.28.17), metoxadiazone (O.28.18), piperonyl butoxide (O.28.19), pyflubumide (O.28.20), pyridalyl (O.28.21), tioxazafen (O.28.22), 11-(4-chloro-2,6-dimethylphenyl)-12-hydroxy-1,4-dioxa-9-azadispiro[4.2.4.2]-tetradec-11-en-10-one, 3-(4'-fluoro-2,4-dimethylbiphenyl-3-yl)-4-hydroxy-8-oxa-1-azaspiro[4.5]dec-3-en-2-one, 1-[2-fluoro-4-methyl-5-[(2,2,2-trifluoroethyl)sulfinyl]phenyl]-3-(trifluoromethyl)-1H-1,2,4-triazole-5-amine (O.28.23), *Bacillus firmus* I-1582 (O.28.24), flupyrimin (O.28.25), fluazaindolizine (O.28.26), 4-[5-(3,5-dichlorophenyl)-5-(trifluoromethyl)-4H-isoxazol-3-yl]-2-methyl-N-(1-oxothietan-3-yl)benzamide (O.28.27), fluxametamide (O.28.28), 5-[3-[2,6-dichloro-4-(3,3-dichloroallyloxy)phenoxy]propoxy]-1H-pyrazole (O.28.1), 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide (O.28.29), 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide (O.28.30), N-[5-[[2-chloro-6-cyano-4-[1,2,2,3,3,3-hexafluoro-1-(trifluoromethyl)propyl]-phenyl]carbamoyl]-2-cyano-phenyl]-4-cyano-2-methyl-benzamide (O.28.31), N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide (O.28.32), N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide (O.28.33), 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide (O.28.34), 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide (O.28.35), N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide (O.28.36); 2-(1,3-dioxan-2-yl)-6-[2(3-pyridinyl)-5-thiazolyl]-pyridine (O.28.37), 2-[6-[2-(5-fluoro-3-pyridinyl)-5-thiazolyl]-2-pyridinyl]-pyrimidine (O.28.38), 2-[6-[2-(3-pyridinyl)-5-thiazolyl]-2-pyridinyl]-pyrimidine (O.28.39), N-methylsulfonyl-6-[2-(3-pyridyl)thiazol-5-yl]pyridine-2-carboxamide (O.28.40), N-methylsulfonyl-6-[2-(3-pyridyl)thiazol-5-yl]pyridine-2-carboxamide (O.28.41), 1-[(6-chloro-3-pyridinyl)methyl]-1,2,3,5,6,7-hexahydro-5-methoxy-7-methyl-8-nitro-imidazo[1,2-a]pyridine (O.28.42), 1-[(6-chloropyridin-3-yl)methyl]-7-methyl-8-nitro-1,2,3,5,6,7-hexahydroimidazo[1,2-a]pyridin-5-ol (O.28.43), 1-isopropyl-N,5-dimethyl-N-pyridazin-4-yl-pyrazole-4-carboxamide (O.28.44), 1-(1,2-dimethylpropyl)-N-ethyl-5-methyl-N-pyridazin-4-yl-pyrazole-4-carboxamide (O.28.45), N,5-dimethyl-N-pyridazin-4-yl-1-(2,2,2-trifluoro-1-methyl-ethyl) pyrazole-4-carboxamide (O.28.46), 1-[1-(1-cyanocyclopropyl)ethyl]-N-ethyl-5-methyl-N-pyridazin-4-yl-pyrazole-4-carboxamide (O.28.47), N-ethyl-1-(2-fluoro-1-methyl-propyl)-5-meth-yl-N-pyridazin-4-yl-pyrazole-4-carboxamide (O.28.48), 1-(1,2-dimethylpropyl)-N,5-dimethyl-N-pyridazin-4-ylpyrazole-4-carboxamide (O.28.49), 1-[1-(1-cyanocyclopropyl)ethyl]-N,5-dimethyl-N-pyridazin-4-yl-pyrazole-4-carboxamide (O.28.50), N-ethyl-1-(2-fluoro-1-methyl-propyl)-5-methyl-N-pyridazin-4-yl-pyrazole-4-carboxamide (O.28.51), 1-(4,4-difluorocyclohexyl)-N-ethyl-5-methyl-N-pyridazin-4-yl-pyrazole-4-carboxamide (O.28.52), 1-(4,4-difluorocyclohexyl)-N,5-dimethyl-N-pyridazin-4-yl-pyrazole-4-carboxamide (O.28.53), N-(1-methylethyl)-2-(3-pyridinyl)-2H-indazole-4-carboxamide (O.28.54), N-cyclopropyl-2-(3-pyridinyl)-2H-indazole-4-carboxamide (O.28.55), N-cyclohexyl-2-(3-pyridinyl)-2H-indazole-4-carboxamide (O.28.56), 2-(3-pyridinyl)-N-(2,2,2-trifluoroethyl)-2H-indazole-4-carboxamide (O.28.57), 2-(3-pyridinyl)-N-[(tetrahydro-2-furanyl)methyl]-2H-indazole-5-carboxamide (O.28.58), methyl 2-[[2-(3-pyridinyl)-2H-indazol-5-yl]carbonyl]hydrazinecarboxylate (O.28.59), N-[(2,2-difluorocyclopropyl)methyl]-2-(3-pyridinyl)-2H-indazole-5-carboxamide (O.28.60), N-(2,2-difluoropropyl)-2-(3-pyridinyl)-2H-indazole-5-carboxamide (O.28.61), 2-(3-pyridinyl)-N-(2-pyrimidinylmethyl)-2H-indazole-5-carboxamide (O.28.62), N-[(5-methyl-2-pyrazinyl)-methyl]-2-(3-pyridinyl)-2H-indazole-5-carboxamide (O.28.63), tyclopyrazoflor (O.28.64), sarolaner (O.28.65), lotilaner (O.28.66), N-[4-chloro-3-[[phenylmethyl)amino]carbonyl]phenyl]-1-methyl-3-(1,1,2,2,2-pentafluoroethyl)-4-(trifluoromethyl)-1H-pyrazole-5-carboxamide (O.28.67), M.UN.22a 2-(3-ethylsulfonyl-2-pyridyl)-3-methyl-6-(trifluoromethyl)imidazo[4,5-b]pyridine (O.28.68), 2-[3-ethylsulfonyl-5-(trifluoromethyl)-2-pyridyl]-3-methyl-6-(trifluoromethyl)imidazo[4,5-b]pyridine (O.28.69), 4-[5-(3,5-dichlorophenyl)-5-(trifluoromethyl)-4H-isoxazol-3-yl]-N-[(4R)-2-ethyl-3-oxo-isoxazolidin-4-yl]-2-methyl-benzamide (O.28.70), 4-[5-(3,5-dichloro-4-fluoro-phenyl)-5-(trifluoromethyl)-4H-isoxazol-3-yl]-N-[(4R)-2-ethyl-3-oxo-isoxazolidin-4-yl]-2-methyl-benzamide (O.28.71), N-[4-chloro-3-(cyclopropylcarbamoyl)phenyl]-2-methyl-5-(1,1,2,2,2-pentafluoroethyl)-4-(trifluoromethyl)pyrazole-3-carboxamide (O.28.72), N-[4-chloro-3-[(1-cyanocyclopropyl)-carbamoyl]phenyl]-2-methyl-5-(1,1,2,2,2-pentafluoroethyl)-4-(trifluoromethyl)pyrazole-3-carboxamide (O.28.73), acynonapyr (O.28.74), benzpyrimoxan (O.28.75), chloro-N-(1-cyano-cyclopropyl)-5-[1-[2-methyl-5-(1,1,2,2,2-pentafluoro-ethyl)-4-(trifluoromethyl)pyrazol-3-yl]pyrazol-4-yl]benzamide (O.28.76), oxazosulfyl (O.28.77), [(2S,3R,4R,5S,6S)-3,5-dimethoxy-6-methyl-4-propoxy-tetrahydropyran-2-yl]-N-[4-[1-[4-(trifluoromethoxy)phenyl]-1,2,4-triazol-3-yl]phenyl]carbamate (O.28.78), [(2S,3R,4R,5S,6S)-3,4,5-trimethoxy-6-methyl-tetrahydropyran-2-yl]-N-[4-[1-[4-(trifluoromethoxy)phenyl]-1,2,4-triazol-3-yl]phenyl]-carbamate (O.28.79), [(2 S,3R,4R,5 S,6 S)-3,5-dimethoxy-6-methyl-4-propoxytetrahydropyran-2-yl]-N-[4-[1-[4-(1,1,2,2,2-pentafluoroethoxy)phenyl]-1,2,4-triazol-3-yl]phenyl] carbamate (O.28.80), [(2S,3R,4R,5S,6S)-3,4,5-trimethoxy-6-methyl-tetrahydropyran-2-yl]-N-[4-[1-[4-(1,1,2,2,2-pentafluoroethoxy)phenyl]-1,2,4-triazol-3-yl] phenyl]-carbamate (O.28.81), (2Z)-3-(2-isopropylphenyl)-2-[(E)-[4-[1-[4-(1,1,2,2,2-pentafluoroethoxy)phenyl]-1,2,4-triazol-3-yl]phenyl] methylenehydrazono]thiazolidin-4-one (O.28.82).

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441, JP2015089883, JP2015120675, WO2015119246, WO2011135827, WO2012084812).

The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day.

In the binary mixtures and compositions according to the invention the weight ratio of the component 1) and the component 2) generally depends from the properties of the active components used, usually it is in the range of from 1:10,000 to 10,000:1, often it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1. According to further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Accordingly, the present invention furthermore relates to mixtures comprising one compound of the formula I (component 1, a group represented by the expression "(I)") and one pesticide II (component 2), wherein pesticide II is an active ingredients selected from the groups A) to O) defined above.

Further embodiments B-1 to B-684 listed in Table B below relate to mixtures comprising as active components one of the in the present specification individualized compounds of the formula I, which is selected from the group of compounds I.A.A-1 to I.A.A-72, I.B.A-1 to I.B.A-72, I.C.A-1 to I.C.A-72 as defined in tables 1 to 3 or from compounds Ex-1 to Ex-31 as defined in tables C.1, C.2 and C.3 (component 1, a group represented by the expression "(I)"), and one pesticide II selected from the groups A) to O) as defined herein (component 2, for example, (A.1.1) or azoxystrobin, in embodiment B-1).

Preferably, the compositions described in Table B comprise the active components in synergistically effective amounts.

TABLE B

B-1: (I) + (A.1.1), B-2: (I) + (A.1.2), B-3: (I) + (A.1.3), B-4: (I) + (A.1.4), B-5: (I) + (A.1.5), B-6: (I) + (A.1.6), B-7: (I) + (A.1.7), B-8: (I) + (A.1.8), B-9: (I) + (A.1.9), B-10: (I) + (A.1.10), B-11: (I) + (A.1.11), B-12: (I) + (A.1.12), B-13: (I) + (A.1.13), B-14: (I) + (A.1.14), B-15: (I) + (A.1.15), B-16: (I) + (A.1.16), B-17: (I) + (A.1.17), B-18: (I) + (A.1.18), B-19: (I) + (A.1.19), B-20: (I) + (A.1.20), B-21: (I) + (A.1.21), B-22: (I) + (A.1.21a), B-23: (I) + (A.1.22), B-24: (I) + (A.1.25), B-25: (I) + (A.1.34), B-26: (I) + (A.1.35), B-27: (I) + (A.1.36), B-28: (I) + (A.1.37), B-29: (I) + (A.1.38), B-30: (I) + (A.2.1), B-31: (I) + (A.2.2), B-32: (I) + (A.2.3), B-33: (I) + (A.2.4), B-34: (I) + (A.2.5), B-35: (I) + (A.3.1), B-36: (I) + (A.3.2), B-37: (I) + (A.3.3), B-38: (I) + (A.3.4), B-39: (I) + (A.3.5), B-40: (I) + (A.3.6), B-41: (I) + (A.3.7), B-42: (I) + (A.3.8), B-43: (I) + (A.3.9), B-44: (I) + (A.3.10), B-45: (I) + (A.3.11), B-46: (I) + (A.3.12), B-47: (I) + (A.3.13), B-48: (I) + (A.3.14), B-49: (I) + (A.3.15), B-50: (I) + (A.3.16), B-51: (I) + (A.3.17), B-52: (I) + (A.3.18), B-53: (I) + (A.3.19), B-54: (I) + (A.3.20), B-55: (I) + (A.3.21), B-56: (I) + (A.3.22), B-57: (I) + (A.3.23), B-58: (I) + (A.3.24), B-59: (I) + (A.3.25), B-60: (I) + (A.3.26), B-61: (I) + (A.3.27), B-62: (I) + (A.3.28), B-63: (I) + (A.3.30), B-64: (I) + (A.3.31), B-65: (I) + (A.3.32), B-66: (I) + (A.3.33), B-67: (I) + (A.3.34), B-68: (I) + (A.3.35), B-69: (I) + (A.3.36), B-70: (I) + (A.3.37), B-71: (I) + (A.3.38), B-72: (I) + (A.3.39), B-73: (I) + (A.4.1), B-74: (I) + (A.4.2), B-75: (I) + (A.4.3), B-76: (I) + (A.4.4), B-77: (I) + (A.4.5), B-78: (I) + (A.4.6), B-79: (I) + (A.4.7), B-80: (I) + (A.4.8), B-81: (I) + (A.4.9), B-82: (I) + (A.4.10), B-83: (I) + (A.4.11), B-84: (I) + (A.4.12), B-85: (I) + (B.1.1), B-86: (I) + (B.1.2), B-87: (I) + (B.1.3), B-88: (I) + (B.1.4), B-89: (I) + (B.1.5), B-90: (I) + (B.1.6), B-91: (I) + (B.1.7), B-92: (I) + (B.1.8), B-93: (I) + (B.1.9), B-94: (I) + (B.1.10), B-95: (I) + (B.1.11), B-96: (I) + (B.1.12), B-97: (I) + (B.1.13), B-98: (I) + (B.1.14), B-99: (I) + (B.1.15), B-100: (I) + (B.1.16), B-101: (I) + (B.1.17), B-102: (I) + (B.1.18), B-103: (I) + (B.1.19), B-104: (I) + (B.1.20), B-105: (I) + (B.1.21), B-106: (I) + (B.1.22), B-107: (I) + (B.1.23), B-108: (I) + (B.1.24), B-109: (I) + (B.1.25), B-110: (I) + (B.1.26), B-111: (I) + (B.1.27), B-112: (I) + (B.1.28), B-113: (I) + (B.1.29), B-114: (I) + (B.1.30), B-115: (I) + (B.1.31), B-116: (I) + (B.1.32), B-117: (I) + (B.1.37), B-118: (I) + (B.1.38), B-119: (I) + (B.1.39), B-120: (I) + (B.1.40), B-121: (I) + (B.1.41), B-122: (I) + (B.1.42), B-123: (I) + (B.1.43), B-124: (I) + (B.1.44), B-125: (I) + (B.1.45), B-126: (I) + (B.1.46), B-127: (I) + (B.1.47), B-128: (I) + (B.1.48), B-129: (I) + (B.1.49), B-130: (I) + (B.1.50), B-131: (I) + (B.1.51), B-132: (I) + (B.1.52), B-133: (I) + (B.2.1), B-134: (I) + (B.2.2), B-135: (I) + (B.2.3), B-136: (I) + (B.2.4), B-137: (I) + (B.2.5), B-138: (I) + (B.2.6), B-139: (I) + (B.2.7), B-140: (I) + (B.2.8), B-141: (I) + (B.3.1), B-142: (I) + (B.4.1), B-143: (I) + (C.1.1), B-144: (I) + (C.1.2), B-145: (I) + (C.1.3), B-146: (I) + (C.1.4), B-147: (I) + (C.1.5), B-148: (I) + (C.1.6), B-149: (I) + (C.1.7), B-150: (I) + (C.2.1), B-151: (I) + (C.2.2), B-152: (I) + (C.2.3), B-153: (I) + (C.2.4), B-154: (I) + (C.2.5), B-155: (I) + (C.2.6), B-156: (I) + (C.2.7), B-157: (I) + (C.2.8), B-158: (I) + (D.1.1), B-159: (I) + (D.1.2), B-160: (I) + (D.1.3), B-161: (I) + (D.1.4), B-162: (I) + (D.1.5), B-163: (I) + (D.1.6), B-164: (I) + (D.1.7), B-165: (I) + (D.1.8), B-166: (I) + (D.1.9), B-167: (I) + (D.1.10), B-168: (I) + (D.1.11), B-169: (I) + (D.1.12), B-170: (I) + (D.1.13), B-171: (I) + (D.1.14), B-172: (I) + (D.1.15), B-173: (I) + (D.1.16), B-174: (I) + (D.2.1), B-175: (I) + (D.2.2), B-176: (I) + (D.2.3), B-177: (I) + (D.2.4), B-178: (I) + (D.2.5), B-179: (I) + (D.2.6), B-180: (I) + (D.2.7), B-181: (I) + (E.1.1), B-182: (I) + (E.1.2), B-183: (I) + (E.1.3), B-184: (I) + (E.2.1), B-185: (I) + (E.2.2), B-186: (I) + (E.2.3), B-187: (I) + (E.2.4), B-188: (I) + (E.2.5), B-189: (I) + (E.2.6), B-190: (I) + (F.1.1), B-191: (I) + (F.1.2), B-192: (I) + (F.1.3), B-193: (I) + (F.1.4), B-

TABLE B-continued

194: (I) + (F.1.5), B-195: (I) + (F.2.1), B-196: (I) + (G.1.1), B-197: (I) + (G.1.2), B-198: (I) + (G.1.3), B-199: (I) + (G.1.4), B-200: (I) + (G.2.1), B-201: (I) + (G.2.2), B-202: (I) + (G.2.3), B-203: (I) + (G.2.4), B-204: (I) + (G.2.5), B-205: (I) + (G.2.6), B-206: (I) + (G.2.7), B-207: (I) + (G.3.1), B-208: (I) + (G.3.2), B-209: (I) + (G.3.3), B-210: (I) + (G.3.4), B-211: (I) + (G.3.5), B-212: (I) + (G.3.6), B-213: (I) + (G.3.7), B-214: (I) + (G.4.1), B-215: (I) + (G.5.1), B-216: (I) + (G.5.2), B-217: (I) + (G.5.3), B-218: (I) + (G.5.4), B-219: (I) + (G.5.5), B-220: (I) + (G.5.6), B-221: (I) + (G.5.7), B-222: (I) + (G.5.8), B-223: (I) + (G.5.9), B-224: (I) + (G.5.10), B-225: (I) + (G.5.11), B-226: (I) + (H.1.1), B-227: (I) + (H.1.2), B-228: (I)+ (H.1.3), B-229: (I) + (H.1.4), B-230: (I) + (H.1.5), B-231: (I) + (H.1.6), B-232: (I) + (H.1.7), B-233: (I) + (H.2.1), B-234: (I) + (H.2.2), B-235: (I) + (H.2.3), B-236: (I) + (H.2.4), B-237: (I) + (H.2.5), B-238: (I) + (H.2.6), B-239: (I) + (H.2.7), B-240: (I) + (H.2.8), B-241: (I) + (H.2.9), B-242: (I) + (H.3.1), B-243: (I) + (H.3.2), B-244: (I) + (H.3.3), B-245: (I) + (H.3.4), B-246: (I) + (H.3.5), B-247: (I) + (H.3.6), B-248: (I) + (H.3.7), B-249: (I) + (H.3.8), B-250: (I) + (H.3.9), B-251: (I) + (H.3.10), B-252: (I) + (H.3.11), B-253: (I) + (H.4.1), B-254: (I) + (H.4.2), B-255: (I) + (H.4.3), B-256: (I) + (H.4.4), B-257: (I) + (H.4.5), B-258: (I) + (H.4.6), B-259: (I) + (H.4.7), B-260: (I) + (H.4.8), B-261: (I) + (H.4.9), B-262: (I) + (H.4.10), B-263: (I) + (I.1.1), B-264: (I) + (I.1.2), B-265: (I) + (I.2.1), B-266: (I) + (I.2.2), B-267: (I) + (I.2.3), B-268: (I) + (I.2.4), B-269: (I) + (I.2.5), B-270: (I) + (J.1.1), B-271: (I) + (J.1.2), B-272: (I) + (J.1.3), B-273: (I) + (J.1.4), B-274: (I) + (J.1.5), B-275: (1) + (J.1.6), B-276: (I) + (J.1.7), B-277: (I) + (J.1.8), B-278: (I) + (J.1.9), B-279: (I) + (J.1.10), B-280: (I) + (K.1.1), B-281: (I) + (K.1.2), B-282: (I) + (K.1.3), B-283: (I) + (K.1.4), B-284: (I) + (K.1.5), B-285: (I) + (K.1.6), B-286: (I) + (K.1.7), B-287: (I) + (K.1.8), B-288: (I) + (K.1.9), B-289: (I) + (K.1.10), B-290: (I) + (K.1.11), B-291: (I) + (K.1.12), B-292: (I) + (K.1.13), B-293: (I) + (K.1.14), B-294: (I) + (K.1.15), B-295: (I) + (K.1.16), B-296: (I) + (K.1.17), B-297: (I) + (K.1.18), B-298: (I) + (K.1.19), B-299: (I) + (K.1.20), B-300: (I) + (K.1.21), B-301: (I) + (K.1.22), B-302: (I) + (K.1.23), B-303: (I) + (K.1.24), B-304: (I) + (K.1.25), B-305: (I) + (K.1.26), B-306: (I) + (K.1.27), B-307: (I) + (K.1.28), B-308: (I) + (K.1.29), B-309: (I) + (K.1.30), B-310: (I) + (K.1.31), B-311: (I) + (K.1.32), B-312: (I) + (K.1.33), B-313: (I) + (K.1.34), B-314: (I) + (K.1.35), B-315: (I) + (K.1.36), B-316: (I) + (K.1.37), B-317: (I) + (K.1.38), B-318: (I) + (K.1.39), B-319: (I) + (K.1.40), B-320: (I) + (K.1.41), B-321: (I) + (K.1.42), B-322: (I) + (K.1.43), B-323: (I) + (K.1.44), B-324: (I) + (K.1.45), B-325: (I) + (K.1.46), B-326: (I) + (K.1.47), B-327: (I) + (K.1.48), B-328: (I) + (K.1.49), B-329: (I) + (K.1.50), B-330: (I) + (K.1.51), B-331: (I) + (K.1.52), B-332: (I) + (K.1.53), B-333: (I) + (K.1.54), B-334: (I) + (O.1.1), B-335: (I) + (O.1.2), B-336: (I) + (O.1.3), B-337: (I) + (O.1.4), B-338: (I) + (O.1.5), B-339: (I) + (O.1.6), B-340: (I) + (O.1.7), B-341: (I) + (O.1.8), B-342: (I) + (O.1.9), B-343: (I) + (O.1.10), B-344: (I) + (O.1.11), B-345: (I) + (O.1.12), B-346: (I) + (O.1.13), B-347: (I) + (O.1.14), B-348: (I) + (O.1.15), B-349: (I) + (O.1.16), B-350: (I) + (O.1.17), B-351: (I) + (O.1.18), B-352: (I) + (O.1.19), B-353: (I) + (O.1.20), B-354: (I) + (O.1.21), B-355: (I) + (O.1.22), B-356: (I) + (O.1.23), B-357: (I) + (O.1.24), B-358: (I) + (O.1.25), B-359: (I) + (O.1.26), B-360: (I) + (O.1.27), B-361: (I) + (O.1.28), B-362: (I) + (O.1.29), B-363: (I) + (O.1.30), B-364: (I) + (O.1.31), B-365: (I) + (O.1.32), B-366: (I) + (O.1.33), B-367: (I) + (O.1.34), B-368: (I) + (O.1.35), B-369: (I) + (O.1.36), B-370: (I) + (O.1.37), B-371: (I) + (O.1.38), B-372: (I) + (O.1.39), B-373: (I) + (O.1.40), B-374: (I) + (O.1.41), B-375: (I) + (O.1.42), B-376: (I) + (O.1.43), B-377: (I) + (O.1.44), B-378: (I) + (O.1.45), B-379: (I) + (O.1.46), B-380: (I) + (O.1.47), B-381: (I) + (O.1.48), B-382: (I) + (O.1.49), B-383: (I) + (O.1.50), B-384: (I) + (O.1.51), B-385: (I) + (O.1.52), B-386: (I) + (O.1.53), B-387: (I) + (O.1.54), B-388: (I) + (O.1.55), B-389: (I) + (O.1.56), B-390: (I) + (O.1.57), B-391: (I) + (O.1.58), B-392: (I) + (O.1.59), B-393: (I) + (O.1.60), B-394: (I) + (O.1.61), B-395: (I) + (O.1.62), B-396: (I) + (O.1.63), B-397: (I) + (O.1.64), B-398: (I) + (O.1.65), B-399: (I) + (O.1.66), B-400: (I) + (O.1.67), B-401: (I) + (O.1.68), B-402: (I) + (O.1.69), B-403: (I) + (O.1.70), B-404: (I) + (O.1.71), B-405: (I) + (O.1.72), B-406: (I) + (O.1.73), B-407: (I) + (O.1.74), B-408: (I) + (O.1.75), B-409: (I) + (O.1.76), B-410: (I) + (O.1.77), B-411: (I) + (O.1.78), B-412: (I) + (O.1.79), B-413: (I) + (O.1.80), B-414: (I) + (O.1.81), B-415: (I) + (O.1.82), B-416: (I) + (O.1.83), B-417: (I) + (O.1.84), B-418: (I) + (O.1.85), B-419: (I) + (O.1.86), B-420: (I) + (O.1.87), B-421: (I) + (O.1.88), B-422: (I) + (O.1.89), B-423: (I) + (O.1.90), B-424: (I) + (O.1.91), B-425: (I) + (O.2.1), B-426: (I) + (O.2.2), B-427: (I) + (O.2.3), B-428: (I) + (O.2.4), B-429: (I) + (O.2.5), B-430: (I) + (O.2.6), B-431: (I) + (O.2.7), B-432: (I) + (O.3.1), B-433: (I) + (O.3.2), B-434: (I) + (O.3.3), B-435: (I) + (O.3.4), B-436: (I) + (O.3.5), B-437: (I) + (O.3.6), B-438: (I) + (O.3.7), B-439: (I) + (O.3.8), B-440: (I) + (O.3.9), B-441: (I) + (O.3.10), B-442: (I) + (O.3.11), B-443: (I) + (O.3.12), B-444: (I) + (O.3.13), B-445: (I) + (O.3.14), B-446: (I) + (O.3.15), B-447: (I) + (O.3.16), B-448: (I) + (O.3.17), B-449: (I) + (O.3.18), B-450: (I) + (O.3.19), B-451: (I) + (O.3.20), B-452: (I) + (O.3.21), B-453: (I) + (O.3.22), B-454: (I) + (O.3.23), B-455: (I) + (O.3.24), B-456: (I) + (O.3.25), B-457: (I) + (O.3.26), B-458: (I) + (O.3.27), B-459: (I) + (O.3.28), B-460: (I) + (O.3.29), B-461: (I) + (O.3.30), B-462: (I) + (O.3.31), B-463: (I) + (O.3.32), B-464: (I) + (O.3.33), B-465: (I) + (O.3.34), B-466: (I) + (O.3.35), B-467: (I) + (O.3.36), B-468: (I) + (O.3.37), B-469: (I) + (O.3.38), B-470: (I) + (O.3.39), B-471: (I) + (O.3.40), B-472: (I) + (O.3.41), B-473: (I) + (O.3.42), B-474: (I) + (O.3.43), B-475: (I) + (O.3.44), B-476: (I) + (O.3.45), B-477: (I) + (O.3.46), B-478: (I) + (O.3.47), B-479: (I) + (O.3.48), B-480: (I) + (O.3.49), B-481: (I) + (O.3.50), B-482: (I) + (O.3.51), B-483: (I) + (O.3.52), B-484: (I) + (O.4.1), B-485: (I) + (O.4.2), B-486: (I) + (O.4.3), B-487: (I) + (O.4.4), B-488: (I) + (O.4.5), B-489: (I) + (O.4.6), B-490: (I) + (O.4.7), B-491: (I) + (O.4.8), B-492: (I) + (O.4.9), B-493: (I) + (O.4.10), B-494: (I) + (O.4.11), B-495: (I) + (O.4.12), B-496: (I) + (O.4.13), B-497: (I) + (O.4.14), B-498: (I) + (O.4.15), B-499: (I) + (O.5.1), B-500: (I) + (O.5.2), B-501: (I) + (O.6.1), B-502: (I) + (O.6.2), B-503: (I) + (O.6.3), B-504: (I) + (O.6.4), B-505: (I) + (O.6.5), B-506: (I) + (O.7.1), B-507: (I) + (O.7.2), B-508: (I) + (O.7.3), B-509: (I) + (O.7.4), B-510: (I) + (O.7.5), B-511: (I) + (O.8.1), B-512: (I) + (O.8.2), B-513: (I) + (O.8.3), B-514: (I) + (O.8.4), B-515: (I) + (O.8.5), B-516: (I) + (O.9.1), B-517: (I) + (O.9.2), B-518: (I) + (O.9.3), B-519: (I) + (O.10.1), B-520: (I) + (O.10.2), B-521: (I) + (O.10.3), B-522: (I) + (O.10.4), B-523: (I) + (O.11.1), B-524: (I) + (O.11.2), B-525: (I) + (O.11.3), B-526: (I) + (O.11.4), B-527: (I) + (O.11.5), B-528: (I) + (O.11.6), B-529: (I) + (O.11.7), B-530: (I) + (O.11.8), B-531: (I) + (O.11.9), B-532: (I) +

TABLE B-continued (O.11.10), B-533: (I) + (O.11.11), B-534: (I) + (O.11.12), B-535: (I) + (O.11.13), B-536: (I) + (O.12.1), B-537: (I) + (O.12.2), B-538: (I) + (O.12.3), B-539: (I) + (O.12.4), B-540: (I) + (O.12.5), B-541: (I) + (O.12.6), B-542: (I) + (O.13.1), B-543: (I) + (O.13.2), B-544: (I) + (O.13.3), B-545: (I) + (O.14.1), B-546: (I) + (O.14.2), B-547: (I) + (O.14.3), B-548: (I) + (O.14.4), B-549: (I) + (O.15.1), B-550: (I) + (O.15.2), B-551: (I) + (O.15.3), B-552: (I) + (O.15.4), B-553: (I) + (O.15.5), B-554: (I) + (O.15.6), B-555: (I) + (O.15.7), B-556: (I) + (O.15.8), B-557: (I) + (O.15.9), B-558: (I) + (O.15.10), B-559: (I) + (O.15.11), B-560: (I) + (O.16.1), B-561: (I) + (O.17.1), B-562: (I) + (O.18.1), B-563: (I) + (O.18.2), B-564: (I) + (O.18.3), B-565: (I) + (O.18.4), B-566: (I) + (O.18.5), B-567: (I) + (O.19.1), B-568: (I) + (O.20.1), B-569: (I) + (O.20.2), B-570: (I) + (O.20.3), B-571: (I) + (O.20.4), B-572: (I) + (O.21.1), B-573: (I) + (O.21.2), B-574: (I) + (O.21.3), B-575: (I) + (O.21.4), B-576: (I) + (O.21.5), B-577: (I) + (O.21.6), B-578: (I) + (O.21.7), B-579: (I) + (O.22.1), B-580: (I) + (O.22.2), B-581: (I) + (O.22.3), B-582: (I) + (O.22.4), B-583: (I) + (O.23.1), B-584: (I) + (O.23.2), B-585: (I) + (O.23.3), B-586: (I) + (O.23.4), B-587: (I) + (O.24.1), B-588: (I) + (O.24.2), B-589: (I) + (O.24.3), B-590: (I) + (O.24.4), B-591: (I) + (O.24.5), B-592: (I) + (O.25.1), B-593: (I) + (O.25.2), B-594: (I) + (O.26.1), B-595: (I) + (O.26.2), B-596: (I) + (O.26.3), B-597: (I) + (O.26.4), B-598: (I) + (O.26.5), B-599: (I) + (O.26.6), B-600: (I) + (O.26.7), B-601: (I) + (O.26.8), B-602: (I) + (O.26.9), B-603: (I) + (O.26.10), B-604: (I) + (O.26.11), B-605: (I) + (O.26.12), B-606: (I) + (O.26.13), B-607: (I) + (O.26.14), B-608: (I) + (O.26.15), B-609: (I) + (O.26.16), B-610: (I) + (O.26.17), B-611: (I) + (O.26.18), B-612: (I) + (O.27.1), B-613: (I) + (O.28.1), B-614: (I) + (O.28.2), B-615: (I) + (O.28.3), B-616: (I) + (O.28.4), B-617: (I) + (O.28.5), B-618: (I) + (O.28.7), B-619: (I) + (O.28.8), B-620: (I) + (O.28.9), B-621: (I) + (O.28.10), B-622: (I) + (O.28.11), B-623: (I) + (O.28.12), B-624: (I) + (O.28.13), B-625: (I) + (O.28.14), B-626: (I) + (O.28.15), B-627: (I) + (O.28.16), B-628: (I) + (O.28.17), B-629: (I) + (O.28.18), B-630: (I) + (O.28.19), B-631: (I) + (O.28.20), B-632: (I) + (O.28.21), B-633: (I) + (O.28.22), B-634: (I) + (O.28.23), B-635: (I) + (O.28.24), B-636: (I) + (O.28.25), B-637: (I) + (O.28.26), B-638: (I) + (O.28.27), B-639: (I) + (O.28.28), B-640: (I) + (O.28.29), B-641: (I) + (O.28.30), B-642: (I) + (O.28.31), B-643: (I) + (O.28.42), B-644: (I) + (O.28.43), B-645: (I) + (O.28.44), B-646: (I) + (O.28.45), B-647: (I) + (O.28.46), B-648: (I) + (O.28.47), B-649: (I) + (O.28.48), B-650: (I) + (O.28.49), B-651: (I) + (O.28.50), B-652: (I) + (O.28.51), B-653: (I) + (O.28.52), B-654: (I) + (O.28.53), B-655: (I) + (O.28.54), B-656: (I) + (O.28.55), B-657: (I) + (O.28.56), B-658: (I) + (O.28.57), B-659: (I) + (O.28.58), B-660: (I) + (O.28.59), B-661: (I) + (O.28.60), B-662: (I) + (O.28.61), B-663: (I) + (O.28.62), B-664: (I) + (O.28.63), B-665: (I) + (O.28.64), B-666: (I) + (O.28.65), B-667: (I) + (O.28.66), B-668: (I) + (O.28.67), B-669: (I) + (O.28.68), B-670: (I) + (O.28.69), B-671: (I) + (O.28.70), B-672: (I) + (O.28.71), B-673: (I) + (O.28.72), B-674: (I) + (O.28.73), B-675: (I) + (O.28.74), B-676: (I) + (O.28.75), B-677: (I) + (O.28.76), B-678: (I) + (O.28.77), B-679: (I) + (O.28.78), B-680: (I) + (O.28.79), B-681: (I) + (O.28.80), B-682: (I) + (O.28.81), B-683: (I) + (O.28.82), B-684: (I) + (A.3.29).

The mixtures of active substances can be prepared as compositions comprising besides the active ingredients at least one inert ingredient (auxiliary) by usual means, e. g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. SYNTHESIS EXAMPLES

I.1 the Compounds of Formula Ex-1 to Ex-5 can be Prepared According to the Methods Outlined Below

I.1.1 Synthesis of 4-vinylbenzonitrile

To a solution of 4-bromobenzonitrile (58.0 g, 318 mmol) in a mixture of propan-2-ol/water (600 mL/300 mL) was added potassium vinyltrifluoroborate (42.7 g, 318 mmol), triethylamine (96.7 g, 956 mmol) and [1,1'-Bis(diphenylphosphino)ferrocene]dichloropalladium(II) (5.22 g, 6.37 mmol) at 25° C. Then the reaction was stirred at 100° C. under nitrogen atmosphere for 16 hours. The reaction mixture was concentrated and extracted with methyl tert-butyl ether. The organic layers were combined and concentrated. The crude product was purified by flash chromatography to afford the title compound (26.0 g, 63%) as a yellow oil. $^1$H NMR (CDCl$_3$, 400 MHz): δ [ppm]=5.41 (d, 1H), 5.84 (d, 1H), 6.69 (dd, 1H), 7.44 (d, 2H), 7.52-7.62 (m, 2H).

I.1.2 Synthesis of N'-hydroxy-4-vinyl-benzamidine

To a solution of 4-vinylbenzonitrile (5.0 g, 38.7 mmol) in ethanol (50 mL) hydroxylamine hydrochloride (5.4 g, 77.4 mmol) and triethylamine (11.8 g, 116.1 mmol) were added. Then the reaction was stirred at 70° C. for 8 hours. The mixture was concentrated and the residue was washed with water. Then the solid was concentrated to afford the title compound (2.7 g, 43.0%) as white solid. $^1$H NMR (CDCl$_3$, 400 MHz): δ [ppm]=7.72 (d, 2H), 7.57 (d, 2H), 6.86 (dd, 1H), 5.94 (d, 1H), 5.39 (d, 1H), 3.71 (q, 1H).

I.1.3 Synthesis of 5-(trifluoromethyl)-3-(4-vinylphenyl)-1,2,4-oxadiazole

To a solution of N'-hydroxy-4-vinyl-benzamidine (1.0 g, 6.17 mmol) in N,N-dimethylacetamide (20 mL) was added trifluoroacetic anhydride (2.6 g, 12.3 mmol) dropwise at 0° C. Then the reaction was stirred at 0 to 25° C. for 8 hours. The mixture was poured into a saturated aqueous solution of sodium bicarbonate and extracted with ethyl acetate. Then the organic layers were washed with brine, dried over sodium sulfate, filtered and concentrated. The crude product was purified by flash chromatography to afford the title compound (3.2 g, crude) as yellow solid. $^1$H NMR (CDCl$_3$, 400 MHz): δ [ppm]=8.07 (d, 2H), 7.54 (d, 2H), 6.76 (dd, 1H), 5.88 (d, 1H), 5.40 (d, 1H).

I.1.4 Synthesis of 3-[4-(1-cyclopropylsulfonylaziridin-2-yl)phenyl]-5-(trifluoromethyl)-1,2,4-oxadiazole (Ex-4)

To a solution of 5-(trifluoromethyl)-3-(4-vinylphenyl)-1,2,4-oxadiazole (2.0 g, 8.7 mmol) in acetonitrile (50 mL) was added cyclopropanesulfonamide (2.3 g, 19.2 mmol), (diacetoxyiodo)benzene (3.1 g, 9.6 mmol) and tetrakis(acetonitrile)copper(I) (326 mg, 0.87 mmol). Then the reaction was stirred at 60° C. for 16 hours. The mixture was concentrated and purified by flash chromatography to afford the title compound (710 mg, 22.7%) as a yellow solid. $^1$H NMR (CDCl$_3$, 400 MHz): δ [ppm]=8.14 (d, 2H), 7.52 (d, 2H), 3.76 (dd, 1H), 3.01 (d, 1H), 2.68 (tt, 1H), 2.48 (d, 1H), 1.42-1.26 (m, 2H), 1.20-1.07 (m, 2H)

I.2 the Compounds of Formula Ex-11 to Ex-14 can be Prepared According to the Methods Outlined Below

I.2.1 Synthesis of 3-[4-(oxiran-2-yl)phenyl]-5-(trifluoromethyl)-1,2,4-oxadiazole To a solution of 5-(trifluoromethyl)-3-(4-vinylphenyl)-1,2,4-oxadiazole (45.0 g, 187.5 mmol) in dichloromethane (1.5 L) was added meta-chloroperoxybenzoic acid (85% purity, 76.1 g, 375 mmol) in portions at 25° C. Then the reaction was stirred at 25° C. for 16 hours. The mixture was concentrated to remove approximately 60% of dichloromethane and filtered. Then the filtration was washed with saturated aqueous solutions of sodium bicarbonate. The organic phase was dried over sodium sulfate and concentrated, and purified by flash chromatography to afford the title compound (40.0 g, 83.3%) as a yellow oil. $^1$H NMR (CDCl$_3$, 400 MHz): δ [ppm]=8.16-8.03 (m, 2H), 7.49-7.40 (m, 2H), 3.93 (dd, 1H), 3.21 (dd, 1H), 2.82 (dd, 1H).

I.2.2 Synthesis of 2-azido-1-[4-[5-(trifluoromethyl)-1,2,4-oxadiazol-3-yl]phenyl]ethanol and 2-azido-2-[4-[5-(trifluoromethyl)-1,2,4-oxadiazol-3-yl]phenyl]ethanol To a solution 3-[4-(oxiran-2-yl)phenyl]-5-(trifluoromethyl)-1,2,4-oxadiazole (20.0 g, 78.1 mmol) in methanol (500 mL) was added sodium azide (12.7 g, 195.2 mmol) in water (80 mL), then followed by ammonium chloride (12.5 g, 234.2 mmol) in water (80 mL). Then the reaction was stirred at 25° C. for 16 hours. The mixture was concentrated by removal of 60% of the methanol, then the organic phase was extracted with ethyl acetate. The organic layers were dried over sodium sulfate, filtered and concentrated. The crude product was purified by flash chromatography to afford 2-azido-1-[4-[5-(trifluoromethyl)-1,2,4-oxadiazol-3-yl]phenyl]ethanol (3.5 g, 15.0%) as yellow oil and 2-azido-2-[4-[5-(trifluoromethyl)-1,2,4-oxadiazol-3-yl]phenyl]ethanol (10.0 g, 42.8%) as yellow solid. $^1$H NMR (CDCl$_3$ 400 MHz): δ [ppm]=8.13 (d, 2H), 7.61-7.50 (m, 2H), 5.01-4.92 (m, 1H), 3.51 (d, 2H), 2.79-2.71 (m, 1H). $^1$H NMR (CDCl$_3$, 400 MHz): δ [ppm]=8.21-8.14 (m, 2H), 7.52 (d, 2H), 4.77 (dd, 1H), 3.87-3.75 (m, 2H).

I.2.3 Synthesis of 3-[4-(aziridin-2-yl)phenyl]-5-(trifluoromethyl)-1,2,4-oxadiazole To a solution of 2-azido-1-[4-[5-(trifluoromethyl)-1,2,4-oxadiazol-3-yl]phenyl]ethanol (10.0 g, 33.42 mmol) in acetonitrile (300 mL) was added triphenylphosphine (17.5 g, 66.8 mmol) in portions at 25° C. Then the reaction mixture was stirred at 80° C. for 8 hours. To a solution of 2-azido-2-[4-[5-(trifluoromethyl)-1,2,4-oxadiazol-3-yl]phenyl]ethanol (7.0 g, 23.4 mmol) in acetonitrile (200 mL) was added triphenylphosphine (12.3 g, 46.8 mmol) in portions at 25° C. Then the reaction was stirred at 80° C. for 8 hours. These two reactions were combined and concentrated to remove acetonitrile, the residue was washed with n-hexane. Then the organic layers were concentrated and purified by flash chromatographie to afford the title compound as yellow oil (5.0 g, 34.5%). $^1$H NMR (CDCl$_3$, 400 MHz): δ [ppm]=8.07 (d, 2H), 7.41 (d, 2H), 3.12 (s, 1H), 2.42-2.21 (m, 1H), 1.78 (br s, 1H).

I.2.4 Synthesis of N-methyl-2-[4-[5-(trifluoromethyl)-1,2,4-oxadiazol-3-yl]phenyl]aziridine-1-carboxamide (Ex-13)

To a solution of 3-[4-(aziridin-2-yl)phenyl]-5-(trifluoromethyl)-1,2,4-oxadiazole (300 mg, 1.18 mmol) in tetrahydrofuran (5 mL) was added triethylamine (238 mg, 2.35 mmol) at 0° C. Then acetyl chloride (133 mg, 1.42 mmol) was added to the mixture at 0° C. Then the reaction was stirred at room temperature for 30 minutes. The reaction was poured into a saturated aqueous solution of sodium bicarbonate and extracted with ethyl acetate, dried over sodium sulfate, filtered and concentrated. Then the mixture was purified by flash chromatography to afford the title compound as a yellow solid (250 mg, 71.3%). $^1$H NMR (CDCl$_3$, 400 MHz): δ [ppm]=8.11 (d, 2H), 7.48 (d, 2H), 3.54 (dd, 1H), 2.80 (d, 1H), 2.31 (d, 1H), 2.25-2.17 (m, 3H).

I.3 the Compounds of Formula Ex-15 to Ex-30 can be Prepared According to the Methods Outlined Below

I.3.1 Synthesis of tert-butyl 3-(4-aminophenyl)azetidine-1-carboxylate

Zinc powder (11.1 g, 0.17 mol) and 1,2-dibromoethane (2.9 g, 15.7 mmol) in tetrahydrofuran (100 mL) were stirred at 65° C. under nitrogen atmosphere (15 Psi) for 30 minutes and allowed to cool to 25° C. while stirring. Trimethylsilyl chloride (1.6 g, 14.4 mmol) was then added and the mixture was stirred at 25° C. for 1 hour. A solution of tert-butyl-3-iodoazetidine-1-carboxylate (37.0 g, 0.13 mol) in tetrahydrofuran (100 mL) was then slowly dropped and the reaction mixture allowed to stir at 25° C. under nitrogen atmosphere (15 Psi) for two hours. Another suspension of tris(dibenzylideneacetone)dipalladium(0) (1.2 g, 1.3 mmol) and tri(2-furyl)phosphine (1.2 g, 5.2 mmol) in tetrahydrofuran (50 mL) were stirred at 25° C. under nitrogen atmosphere (15 Psi) for 30 minutes, the prepared organozinc reagent solution was added in, then followed by 4-iodobenzonitrile (30.0 g, 0.13 mol) in tetrahydrofuran (150 mL). The resulting mixture was stirred at 65° C. for 13 hours. The reaction mixture was filtered through a pad of celite and the filter cake was washed with methyl tert-butylether. The filtrate was washed with saturated aqueous solutions of sodium bicarbonate, and brine, dried over sodium sulfate, filtered and concentrated under reduced pressure. The residue was purified by flash chromatography to give the title compound as yellow oil (12.7 g, 37.7%).

$^1$H NMR (CDCl$_3$, 400 MHz): δ [ppm]=7.65 (d, 2H) 7.43 (d, 2H) 4.37 (t, 2H) 3.95 (dd, 2H) 3.72-3.83 (m, 1H) 1.47 (s, 9H).

I.3.2 Synthesis of tert-butyl 3-[4-[(Z)—C,N-dihydroxycarbonimidoyl]phenyl]azetidine-1-carboxylate A solution of tert-butyl 3-(4-aminophenyl)azetidine-1-carboxylate (9.9 g, 38.4 mmol) and hydroxylamine hydrochloride (50% aqueous solution, 5.3 g, 76.8 mmol) in ethanol (150 mL) was stirred at 80° C. for 4 hours. Another reaction of tert-butyl 3-(4-aminophenyl)azetidine-1-carboxylate (3 g, 11.6 mmol) was reacted in the same way. The reaction mixtures were then combined and worked up together. The mixed solution was concentrated in vacuum to remove the solvent. The residue was washed with a mixed solvent of methyl tert-butylether (40 mL) and petroleum ether (160 mL) and filtered. The filter cake was washed with water and filtered. The filter cake was dried in vacuum to give the title compound as a white solid (10.7 g, 73.5%). $^1$H NMR (DMSO-d6, 400 MHz): δ [ppm]=9.60 (s, 1H), 7.65 (d, 2H), 7.33 (d, 2H), 5.78 (s, 2H), 4.24 (br s, 2H), 3.81 (br s, 3H), 1.40 (s, 9H).

I.3.3 Synthesis of tert-butyl 3-[4-[5-(trifluoromethyl)-1,2,4-oxadiazol-3-yl]phenyl]azetidine-1-carboxylate To a solution of tert-butyl 3-[4-[(Z)—C,N-dihydroxycarbonimidoyl]phenyl]azetidine-1-carboxylate (8.7 g, 29.9 mmol) in N,N-dimethylacetamide (80 mL) was added trifluoroacetic anhydride (31.4 g, 149.5 mmol) at 0° C. The mixture was stirred at 0 to 25° C. for 5 hours. The reaction solution was poured into ice-water and extracted with ethyl acetate. The organic phase was washed with water, saturated aqueous solutions of sodium bicarbonate and brine, dried over sodium sulfate, filtered and concentrated. The residue was purified by flash chromatography to give the title compound as a yellow oil (9.2 g, 83.0%). $^1$H NMR (CDCl$_3$, 400 MHz): δ [ppm]=8.04-8.17 (m, 2H), 7.48 (d, 2H), 4.39 (t, 2H), 4.01 (dd, 2H), 3.74-3.87 (m, 1H), 1.41-1.52 (m, 9H).

I.3.4 Synthesis of 3-[4-(azetidin-3-yl)phenyl]-5-(trifluoromethyl)-1,2,4-oxadiazole Hydrochloride To a solution of tert-butyl 3-[4-[5-(trifluoromethyl)-1,2,4-oxadiazol-3-yl]phenyl]azetidine-1-carboxylate (3 g, 8.0 mmol) in ethyl acetate (15 mL) was added hydrochloric acid in ethyl acetate (4M, 15 mL), and the mixture was stirred at 25° C. for 5.5 hours. The mixture was concentrated under reduced pressure to give the title compound as white solid which was used directly without purification (2.4 g, crude HCl salt). $^1$H NMR (DMSO-d6, 400 MHz): δ [ppm]=8.06-8.11 (m, 2H) 7.64-7.74 (m, 2H) 3.92-4.38 (m, 5H).

I.3.5 Synthesis of 1-[3-[4-[5-(trifluoromethyl)-1,2,4-oxadiazol-3-yl]phenyl]azetidin-1-yl]ethenone (Ex-30)

To a solution of 3-[4-(azetidin-3-yl)phenyl]-5-(trifluoromethyl)-1,2,4-oxadiazole hydrochloride (500 mg, 1.9 mmol) and triethylamine (770 mg, 7.6 mmol) in methylene chloride (10 mL) was added acetyl chloride (180 mg, 2.3 mmol) dropwise at 0° C. and the mixture was stirred at 0 to 25° C. for 1 hour. The reaction mixture was poured into water and extracted with dichloromethane. The organic phase was washed with water and brine, dried over sodium sulfate and concentrated. The residue was purified by flash chromatography to give the title compound as a white solid (306 mg, 53%). $^1$H NMR (CDCl$_3$, 400 MHz): δ [ppm]=8.13 (d, 2H), 7.48 (d, 2H), 4.59 (t, 1H), 4.47 (t, 1H), 4.19 (dd, 1H), 4.12 (dd, 1H), 3.86-3.95 (m, 1H), 1.95 (s, 3H).

I.4 the Compounds of Formula Ex-31 can be Prepared According to the Methods Outlined Below

I.4.1 Synthesis of tert-butyl 2-(4-cyanophenyl)azetidine-1-carboxylate

To a mixture of tert-butyl-3-iodoazetidine-1-carboxylate (10.0 g, 35.3 mmol), 4-cyanophenyl)boronic acid (10.4 g, 70.6 mmol), 2-dicyclohexylphosphino-2',6'-dimethoxybiphenyl (2.9 g, 7.06 mmol) and palladium(II) acetate (0.79 g, 3.53 mmol) in acetonitrile (90 mL), a solution of potassium phosphate (22.5 g, 106 mmol) in water (60 mL) was added. Then the resulting mixture was stirred at 100° C. under nitrogen atmosphere (15 psi) for 13 hours. The mixture was filtered through a pad of celite and the filter cake was washed with ethyl acetate. The filtrate was partitioned and the organic phase was washed with brine, dried over sodium sulfate, filtered and concentrated. The residue was purified by flash chromatography to give the title compound as a yellow oil. (5.1 g, 57.3%). $^1$H NMR (CDCl$_3$, 400 MHz): δ [ppm]=7.65 (d, 2H), 7.46 (d, 2H), 5.23 (t, 1H), 3.92-4.07 (m, 2H), 2.60-2.71 (m, 1H), 2.06-2.14 (m, 1H), 1.29-1.48 (m, 9H).

I.4.2 Synthesis of tert-butyl 2-[4-[(Z)—N-hydroxycarbamimidoyl]phenyl]azetidine-1-carboxylate A solution of tert-butyl 2-(4-cyanophenyl)azetidine-1-carboxylate (3.6 g, 14.0 mmol), hydroxylamine (HCl salt, 1.9 g, 28.0 mmol) and triethylamine (4.4 g, 42.0 mmol) in ethanol (40 mL) was stirred at 80° C. for 4 hours. The reaction mixture was concentrated under reduced pressure. The residue was washed with a mixed solvent of methyl tert-butylether and petroleum ether and filtered. The filter cake was washed with water and filtered. The filter cake was dried in vacuum to give the title compound as a white solid (2.8 g, 69%).

$^1$H NMR (DMSO-d6, 400 MHz): δ [ppm]=9.61 (s, 1H), 7.66 (d, 2H), 7.34 (d, 2H), 5.80 (s, 2H), 5.14 (dd, 1H), 3.90 (t, 2H), 2.58-2.65 (m, 1H), 2.02 (s, 1H), 1.15-1.45 (m, 9H).

I.4.3 Synthesis of tert-butyl 2-[4-[5-(trifluoromethyl)-1,2,4-oxadiazol-3-yl]phenyl]azetidine-1-carboxylate To a solution of tert-butyl 2-[4-[(Z)—N'-hydroxycarbamimidoyl]phenyl]azetidine-1-carboxylate (1.8 g, 6.2 mmol) and triethylamine (1.3 g, 12.4 mmol) in N,N-dimethylacetamide (20 mL) was added trifluoroacetic anhydride (6.5 g, 31.0 mmol) at 0° C. The mixture was stirred at 0 to 25° C. for 8 hours. The reaction solution was poured into ice water and extracted with methyl tert-butylether. The organic phase was washed with water and brine, dried over sodium sulfate, filtered and concentrated. The residue was purified by flash chromatography to give the title compound as a yellow oil (0.84 g, 37%). $^1$H NMR (CDCl$_3$, 400 MHz): δ [ppm]=8.12 (d, 2H), 7.52 (d, 2H), 5.27 (br t, 1H), 3.98-4.08 (m, 2H), 2.62-2.72 (m, 1H), 2.09-2.22 (m, 1H), 1.21-1.46 (m, 9H).

I.4.4 Synthesis of 1-[2-[4-[5-(trifluoromethyl)-1,2,4-oxadiazol-3-yl]phenyl]azetidin-1-yl]ethenone (Ex-31)

A mixture of tert-butyl 2-[4-[5-(trifluoromethyl)-1,2,4-oxadiazol-3-yl]phenyl]azetidine-1-carboxylate (600 mg, 1.6 mmol) and 2,6-lutidine (1.0 g, 9.8 mmol) in methylene chloride (10 mL) was cooled to 0° C., then trimethylsilyl trifluoromethanesulfonate (1.4 g, 6.5 mmol) was added dropwise, and the resulting mixture was stirred at 25° C. for 4 hours. The reaction was cooled to 0° C. again, and acetyl chloride (156 mg, 2.0 mmol) was added at 0° C. The reaction was stirred at 0° C. for 0.5 hour. The reaction mixture was poured into water and extracted with methylene chloride. The organic phase was washed with water and brine, dried over sodium sulfate, filtered and concentrated. The residue was purified by flash chromatography to give the title compound as a yellow oil (149 mg, 29%).

$^1$H NMR (CDCl$_3$, 400 MHz): δ [ppm]=8.03-8.23 (m, 2H), 7.42-7.59 (m, 2H), 5.35-5.48 (m, 1H), 4.07-4.31 (m, 2H), 2.71-2.86 (m, 1H), 2.11-2.25 (m, 1H), 1.65-2.02 (m, 3H).

The compounds listed in Tables C.1, C.2 and C.3 were prepared in an analogous manner.

TABLE C.1

Compounds Ex-1 to Ex-14 of formula I.H, wherein the meaning of L and R$^1$ are as defined in each line.

I.H

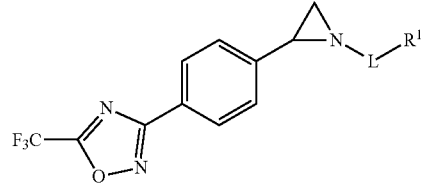

| Ex. no | L | R$^1$ | HPLC R$_t$ (min)* | Melting point (° C.) |
|---|---|---|---|---|
| Ex-1 | —S(=O)$_2$— | C(CH$_3$)$_3$ | 1.312 | 80-86 |
| Ex-2 | —S(=O)$_2$— | CH$_3$ | 1.147 | 121-125 |
| Ex-3 | —S(=O)$_2$— | CH$_2$CH$_3$ | 1.205 | 50-54 |
| Ex-4 | —S(=O)$_2$— | cyclopropyl | 1.220 | 68-79 |
| Ex-5 | —S(=O)$_2$— | CH(CH$_3$)$_2$ | 1.259 | 55-62 |
| Ex-11 | —C(=O)— | CH$_2$CH$_3$ | 1.305 | 34-48 |
| Ex-12 | —C(=O)— | cyclopropyl | 1.285 | 42-45 |
| Ex-13 | —C(=O)— | CH$_3$ | 1.264 | 47-66 |
| Ex-14 | —C(=O)— | CH(CH$_3$)$_2$ | 1.270 | oil |

TABLE C.2

Compounds Ex-15 to Ex-30 of formula I.F, wherein the meaning of L and R$^1$ are as defined in each line.

I.F

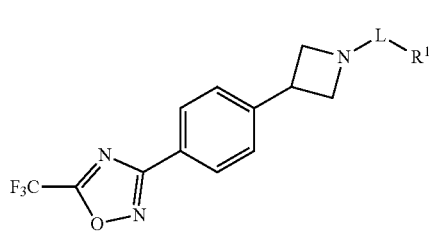

| Ex. no | L | R$^1$ | HPLC R$_t$ (min)* | Melting point (° C.) |
|---|---|---|---|---|
| Ex-15 | —S(=O)— | C(CH$_3$)$_3$ | 1.321 | 72-75 |
| Ex-16 | —S(=O)$_2$— | CH$_3$ | 1.153 | 147-149 |
| Ex-17 | —S(=O)$_2$— | CH$_2$CH$_3$ | 1.215 | 101-102 |

TABLE C.2-continued

Compounds Ex-15 to Ex-30 of formula I.F, wherein the meaning of L and R$^1$ are as defined in each line.

I.F

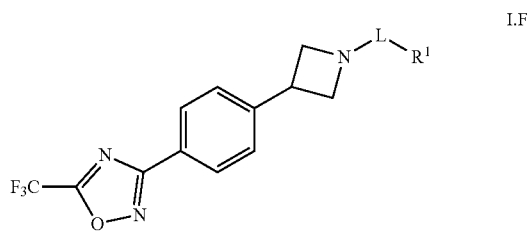

| Ex. no | L | R$^1$ | HPLC R$_t$ (min)* | Melting point (° C.) |
|---|---|---|---|---|
| Ex-18 | —S(=O)$_2$— | CH(CH$_3$)$_2$ | 1.282 | 62-73 |
| Ex-19 | —S(=O)$_2$— | cyclopropyl | 1.225 | 98-100 |
| Ex-20 | —S(=O)$_2$— | C(CH$_3$)$_3$ | 1.343 | — |
| Ex-21 | —C(=O)NH— | CH$_2$CH$_3$ | 1.102 | 163-164 |
| Ex-22 | —C(=O)NH— | CH(CH$_3$)$_2$ | 1.159 | 167-169 |
| Ex-23 | —C(=O)NH— | C(CH$_3$)$_3$ | 1.251 | 121-123 |
| Ex-24 | —C(=O)NH— | CH$_3$ | 1.045 | 137-145 |
| Ex-25 | —C(=O)NH— | cyclopropyl | 1.108 | 143-147; 170-181 |

TABLE C.2-continued

Compounds Ex-15 to Ex-30 of formula I.F, wherein the meaning of L and $R^1$ are as defined in each line.

I.F

| Ex. no | L | $R^1$ | HPLC $R_t$ (min)* | Melting point (° C.) |
|---|---|---|---|---|
| Ex-26 | —C(=O)— | $CH_2CH_3$ | 1.144 | oil |
| Ex-27 | —C(=O)— | $CH(CH_3)_2$ | 1.203 | 87-91 |
| Ex-28 | —C(=O)— | $C(CH_3)_3$ | 1.278 | 130-131 |
| Ex-29 | —C(=O)— | cyclopropyl | 1.172 | 69-71 |
| Ex-30 | —C(=O)— | $CH_3$ | 1.074 | 90-92 |

TABLE C.3

Compound Ex-31 of formula I.G, wherein the meaning of L and $R^1$ are as defined.

I.G

| Ex. no | L | $R^1$ | HPLC $R_t$ (min)* | Melting point (° C.) |
|---|---|---|---|---|
| Ex-31 | —C(=O)— | —$CH_3$ | 1.084 | oil |

*HPLC: High Performance Liquid Chromatography; HPLC-column Kinetex XB C18 1,7μ (50 × 2,1 mm); eluent: acetonitrile/water + 0.1% trifluoroacetic acid (gradient from 5:95 to 100:0 in 1.5 min at 60° C., flow gradient from 0.8 to 1.0 ml/min in 1.5 min). MS: Quadrupol Electrospray Ionisation, 80 V (positive mode). $R_t$: retention time in minutes.

II. BIOLOGICAL EXAMPLES FOR FUNGICIDAL ACTIVITY

The fungicidal action of the compounds of formula I was demonstrated by the following experiments:

A. Glass House Trials

The spray solutions were prepared in several steps: The stock solution were prepared: a mixture of acetone and/or dimethylsulfoxide and the wetting agent/emulsifier Wettol, which is based on ethoxylated alkylphenoles, in a relation (by volume) solvent to emulsifier of 99 to 1, was added to 25 mg of the compound to give a total of 5 ml. Water was then added to total volume of 100 ml. This stock solution was diluted with the described solvent-emulsifier-water mixture to the given concentration.

A.1. Curative Control of Soy Bean Rust on Soy Beans Caused by *Phakopsora pachyrhizi*

Leaves of pot-grown soy bean seedlings were inoculated with spores of *Phakopsora pachyrhizi*. To ensure the success of the artificial inoculation, the plants were transferred to a humid chamber with a relative humidity of about 95% and 20 to 24° C. for 24 hours. The next day the plants were cultivated for 3 days in a greenhouse chamber at 23 to 27° C. and a relative humidity between 60 and 80%. Then the plants were sprayed to run-off with an aqueous suspension, containing the concentration of active ingredient or their mixture as described below. The plants were allowed to air-dry. Then the trial plants were cultivated for 14 days in a greenhouse chamber at 23 to 27° C. and a relative humidity between 60 and 80%. The extent of fungal attack on the leaves was visually assessed as % diseased leaf area.

In this test, the plants which had been treated with 16 ppm of the active compounds Ex-11, Ex-13, Ex-16, Ex-17, Ex-18, Ex-21, Ex-22, Ex-26, Ex-27, Ex-28, Ex-29, Ex-30 and Ex-31 showed a diseased leaf area of at most 18%, whereas the untreated plants showed 100% diseased leaf area.

In this test, the plants which had been treated with 63 ppm of the active compounds Ex-6, Ex-7, Ex-8, Ex-9, Ex-11, Ex-12, Ex-14, and Ex-20 showed a diseased leaf area of at most 4%, whereas the untreated plants showed 100% diseased leaf area.

A.2. Protective Control of Soy Bean Rust on Soy Beans Caused by *Phakopsora pachyrhizi*

Leaves of pot-grown soy bean seedlings were sprayed to run-off with an aqueous suspension, containing the concentration of active ingredient or their mixture as described below. The plants were allowed to air-dry. The trial plants were cultivated for 2 days in a greenhouse chamber at 23 to 27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20 to 24° C. for 24 hours. The trial plants were cultivated for fourteen days in a greenhouse chamber at 23 to 27° C. and a relative humidity between 60 and 80%. The extent of fungal attack on the leaves was visually assessed as % diseased leaf area.

In this test, the plants which had been treated with 16 ppm of the active compounds Ex-15, Ex-16, Ex-17, Ex-18, Ex-19, Ex-21, Ex-22, Ex-23, Ex-26, Ex-27, Ex-28, Ex-29, Ex-30 and Ex-31 showed a diseased leaf area of at most 8%, whereas the untreated plants showed 100% diseased leaf area.

In this test, the plants which had been treated with 16 ppm of the active compounds Ex-9, Ex-11, Ex-12, and Ex-14 showed a diseased leaf area of at most 9%, whereas the untreated plants showed 80% diseased leaf area.

In this test, the plants which had been treated with 63 ppm of the active compounds Ex-2, Ex-3, Ex-5, Ex-6, Ex-7, Ex-8, and Ex-20 showed a diseased leaf area of at most 17%, whereas the untreated plants showed 80% diseased leaf area.

3. Curative Control of Brown Rust on Wheat Caused by *Puccinia recondita*

The first two developed leaves of pot-grown wheat seedling were dusted with spores of *Puccinia recondita*. To ensure the success the artificial inoculation, the plants were transferred to a humid chamber without light and a relative humidity of 95 to 99% and 20 to 24° C. for 24 hours. The next day the plants were cultivated for 3 days in a greenhouse chamber at 20 to 24° C. and a relative humidity between 65 and 70%. Then the plants were sprayed to run-off with an aqueous suspension, containing the concentration of active ingredient or their mixture as described below. The plants could air-dry. Then the trial plants were cultivated for 8 days in a greenhouse chamber at 20 to 24° C. and a relative humidity between 65 and 70%. The extent of fungal attack on the leaves was visually assessed as % diseased leaf area. In this test, the plants which had been treated with 63 ppm of the active compounds Ex-15, Ex-17, Ex-18, Ex-19, Ex-21, Ex-22, Ex-23, Ex-26, Ex-27, Ex-28, Ex-29, Ex-30 and Ex-31 showed a diseased leaf area of at most 8%, whereas the untreated plants showed 90% diseased leaf area.

4. Preventative Control of Brown Rust on Wheat Caused by *Puccinia recondita*

The first two developed leaves of pot-grown wheat seedling were sprayed to run-off with an aqueous suspension, containing the concentration of active ingredient or their mixture as described below. The next day the plants were inoculated with spores of *Puccinia recondita*. To ensure the success the artificial inoculation, the plants were transferred to a humid chamber without light and a relative humidity of 95 to 99% and 20 to 24° C. for 24 hours. Then the trial plants were cultivated for 6 days in a greenhouse chamber at 20 to 24° C. and a relative humidity between 65 and 70%. The extent of fungal attack on the leaves was visually assessed as % diseased leaf area.

In this test, the plants which had been treated with 63 ppm of the active compounds Ex-16, Ex-17, Ex-18, Ex-19, Ex-21, Ex-23, Ex-26, Ex-27, Ex-28, Ex-29 and Ex-30 showed a diseased leaf area of at most 12%, whereas the untreated plants showed 90% diseased leaf area.

In this test, the plants which had been treated with 63 ppm of the active compounds Ex-2, Ex-4, Ex-5, Ex-6, Ex-7, Ex-8, and Ex-20 showed a diseased leaf area of at most 17%, whereas the untreated plants showed 80% diseased leaf area.

The invention claimed is:

1. A compound of the formula I, or the N-oxides, or the agriculturally acceptable salts thereof,

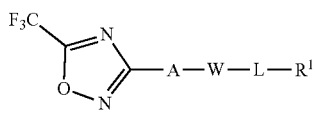

I wherein:
A is phenyl or a 5- or 6-membered aromatic heterocycle; wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein the phenyl ring or the aromatic heterocycle is unsubstituted or substituted with 1, 2, 3 or 4 identical or different groups $R^A$; wherein
  $R^A$ is halogen, cyano, $C_1$-$C_6$-alkyl, $C_1$-$C_6$-haloalkyl, $C_1$-$C_6$-alkoxy or $C_1$-$C_6$-haloalkoxy;
W is a 3- or 4-membered non-aromatic heterocycle containing as ring member atoms besides carbon atoms 1 nitrogen atom; wherein the heterocycle is bound to the group L through said nitrogen ring member atom; and wherein the heterocycle is bound to the group A through one of the carbon ring member atoms; and wherein the heterocycle is further unsubstituted or substituted with 1, 2, 3 or 4 identical or different radicals $R^W$; wherein
  $R^W$ is halogen, cyano, $C_1$-$C_3$-alkyl, $C_1$-$C_3$-haloalkyl, $C_1$-$C_3$-alkoxy or $C_1$-$C_3$-haloalkoxy;
L is —C(=O)—, —C(=S)—, —S(=O)$_p$—, —C(=O)—O-#, —C(=O)NR$^2$-# or —C(=S)NR$^2$-#; wherein #denotes the position, which is bound to radical $R^1$; and wherein
p is 0, 1 or 2;
$R^2$ is hydrogen, formyl, $C_1$-$C_6$-alkyl, $C_2$-$C_6$-alkenyl, $C_2$-$C_6$-alkynyl, $C_3$-$C_5$-cycloalkyl, $C_1$-$C_6$-alkoxy or $C_1$-$C_6$-haloalkyl;
$R^1$ is hydrogen, $C_1$-$C_6$-alkyl, $C_2$-$C_6$-alkenyl, $C_3$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_3$-$C_{11}$-cycloalkyl, $C_3$-$C_{11}$-cycloalkenyl, $C_3$-$C_{11}$-cycloalkyl-$C_1$-$C_4$-alkyl, phenyl-$C_1$-$C_4$-alkyl, heterocyclyl-$C_1$-$C_4$-alkyl, heteroaryl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein 1 or 2 carbon ring member atoms of the heterocycle may be replaced by 1 or 2 groups independently selected from C(=O) and C(=S); and wherein the heterocyclyl group in heterocyclyl-$C_1$-$C_4$-alkyl is a 3- to 10-membered saturated, partially unsaturated, mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein 1 or 2 carbon ring member atoms of the heterocycle may be replaced by 1 or 2 groups independently selected from C(=O) and C(=S); and wherein the heteroaryl group in heteroaryl-$C_1$-$C_4$-alkyl is a 5- or 6-membered aromatic heterocycle, wherein the ring member atoms of the aromatic heterocycle include besides carbon atoms 1, 2, 3 or 4 heteroatoms selected from N, O and S as ring member atoms with the provision that the heterocycle cannot contain 2 contiguous atoms selected from O and S; and wherein any of the aliphatic or cyclic groups $R^1$ are unsubstituted or substituted with 1, 2, 3 or up to the maximum possible number of identical or different groups $R^{1a}$; wherein $R^{1a}$ is halogen, cyano, $C_1$-$C_6$-alkyl, $C_1$-$C_6$-alkoxy or $C_1$-$C_6$-haloalkoxy.

2. The compound according to claim 1, wherein A in compounds of the formula I is phenyl.

3. The compound according to claim 2, which are of the formula I.1, or the N-oxides, or the agriculturally acceptable salts thereof,

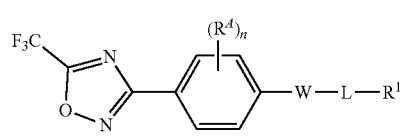

I.1 wherein n is 0, 1 or 2, and wherein the meaning of the variables $R^A$, W, L, $R^1$ and $R^2$, are as defined in claim 1 for compounds of the formula I.

4. The compound according to claim 1, wherein W is selected from the group consisting of W.a, W.b and W.c,

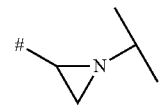

W.a

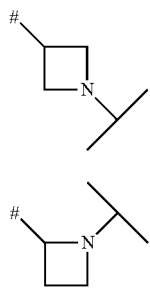

W.b

W.c wherein #denotes the position, which is attached to the group A, and the dashed line denotes the position, which is attached to $R^1$.

5. The compound according to claim 1, wherein L is —C(=O)—.

6. The compound according to claim 1, wherein L is —S(=O)$_2$—.

7. The compound according to claim 1, wherein L is —C(=O)NR$^2$-# or

—C(=S)NR$^2$-#; wherein #denotes the position, which is bound to radical $R^1$.

8. The compound according to claim 1, wherein $R^1$ is hydrogen, $C_1$-$C_6$-alkyl, $C_2$-$C_6$-alkenyl, $C_3$-$C_6$-alkynyl or $C_3$-$C_{11}$-cycloalkyl.

9. The compound according to claim 1, wherein $R^1$ is hydrogen, methyl, ethyl, n-propyl, iso-propyl, n-butyl, iso-butyl, sec-butyl, tert-butyl or cyclopropyl.

10. An intermediate compound of the formula II

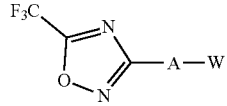

II wherein the variables A, $R^A$, W and $R^W$ are as defined in claim 1 for compounds of the formula I.

11. An intermediate compound of the formula XV

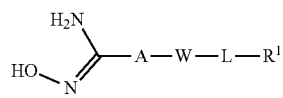

XV wherein the variables A, $R^A$, W, $R^W$, L, p, $R^1$ and $R^2$ are as defined in claim 1 for compounds of the formula I.

12. An agrochemical composition, which comprises an auxiliary and at least one compound as defined in claim 1.

13. An agrochemical composition according to claim 12, further comprising seed, wherein the amount of the at least one compound is from 0.1 g to 10 kg per 100 kg of seed.

14. A method for combating phytopathogenic harmful fungi, which process comprises treating the plants, the soil or seeds to be protected against fungal attack, with an effective amount of at least one compound as defined in claim 1.

* * * * *